United States Patent
Kiersey et al.

(10) Patent No.: US 11,399,935 B2
(45) Date of Patent: Aug. 2, 2022

(54) TRANSCATHETER GUIDEWIRE DELIVERY SYSTEMS, CATHETER ASSEMBLIES FOR GUIDEWIRE DELIVERY, AND METHODS FOR PERCUTANEOUS GUIDEWIRE DELIVERY ACROSS HEART VALVES

(71) Applicant: Medtronic Vascular, Inc., Santa Rosa, CA (US)

(72) Inventors: Simon Kiersey, Ballybrit (IE); Tomas Kelly, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 436 days.

(21) Appl. No.: 16/583,087

(22) Filed: Sep. 25, 2019

(65) Prior Publication Data

US 2020/0015966 A1    Jan. 16, 2020

Related U.S. Application Data

(62) Division of application No. 15/253,377, filed on Aug. 31, 2016, now Pat. No. 10,456,252.

(51) Int. Cl.
*A61F 2/24* (2006.01)
*A61M 25/01* (2006.01)
*A61M 25/00* (2006.01)

(52) U.S. Cl.
CPC .......... *A61F 2/2427* (2013.01); *A61M 25/007* (2013.01); *A61M 25/0108* (2013.01)

(58) Field of Classification Search
CPC .......... A61M 2025/0004; A61M 25/09; A61M 25/09025; A61M 25/09041;
(Continued)

(56) References Cited

U.S. PATENT DOCUMENTS 9,126,018 B1    9/2015   Garrison
2009/0326575 A1   12/2009   Galdonik
(Continued)

FOREIGN PATENT DOCUMENTS

CN    103179921 A    6/2013
CN    105188612 A    12/2015
(Continued)

OTHER PUBLICATIONS

PCT/US2017/049586, Communication Relating to the Results of the Partial International Search, dated Nov. 22, 2017.
(Continued)

*Primary Examiner* — Dung T Ulsh
(74) *Attorney, Agent, or Firm* — Medler Ferro Woodhouse & Mills PLLC

(57) ABSTRACT

Transcatheter guidewire delivery systems, catheter assemblies and associated methods for percutaneous guidewire delivery across heart valves are disclosed herein. A catheter assembly configured in accordance herewith includes an elongated tubular component and an alignment assembly at a distal portion of the tubular component and which is adapted to be located at a target location adjacent a heart valve of a patient. In one embodiment, the alignment assembly deploys to a shape set loop configuration with a side port in an open configuration positioned to allow advancement of a guidewire to exit the catheter in an aligned path with a leaflet coaptation region of the heart valve. In another embodiment, the alignment assembly has a plurality of spaced apart side ports that a guidewire may advance therethrough and toward the heart valve. In some embodiments, a wire guide is used to align the guidewire with a selected side port.

8 Claims, 22 Drawing Sheets

(58) Field of Classification Search
CPC ............ A61M 25/007; A61M 25/0108; A61M 25/0147; A61M 25/0152; A61M 25/0041; A61M 25/0662; A61F 2/2427
See application file for complete search history.

(56) References Cited

U.S. PATENT DOCUMENTS

| | | |
|---|---|---|
| 2010/0185231 A1 | 7/2010 | Lashinski |
| 2012/0010563 A1 | 1/2012 | Ravikumar |
| 2012/0116351 A1 | 5/2012 | Chomas |
| 2014/0155994 A1* | 6/2014 | McDonald ............ A61B 5/1076 623/2.11 |
| 2014/0276602 A1* | 9/2014 | Bonnette ............... A61M 25/01 604/508 |
| 2014/0303497 A1 | 10/2014 | Dalby |
| 2017/0049503 A1 | 2/2017 | Cosman |

FOREIGN PATENT DOCUMENTS

| | | |
|---|---|---|
| CN | 105611903 A | 5/2016 |
| DE | 10201185 A1 | 7/2003 |
| EP | 0154403 A1 | 11/1985 |
| GB | 2399017 A1 | 9/2004 |
| WO | 2011015218 A1 | 2/2011 |
| WO | 2012058586 A2 | 5/2012 |
| WO | 2013057482 A1 | 4/2013 |
| WO | 2014189977 A1 | 11/2014 |
| WO | 2015031898 A2 | 3/2015 |

OTHER PUBLICATIONS

PCT/US2017/049586, PCT communication, dated Mar. 22, 2018.
First Office Action, China Patent Application No. 201780052941.1, dated Jun. 11, 2021.

* cited by examiner

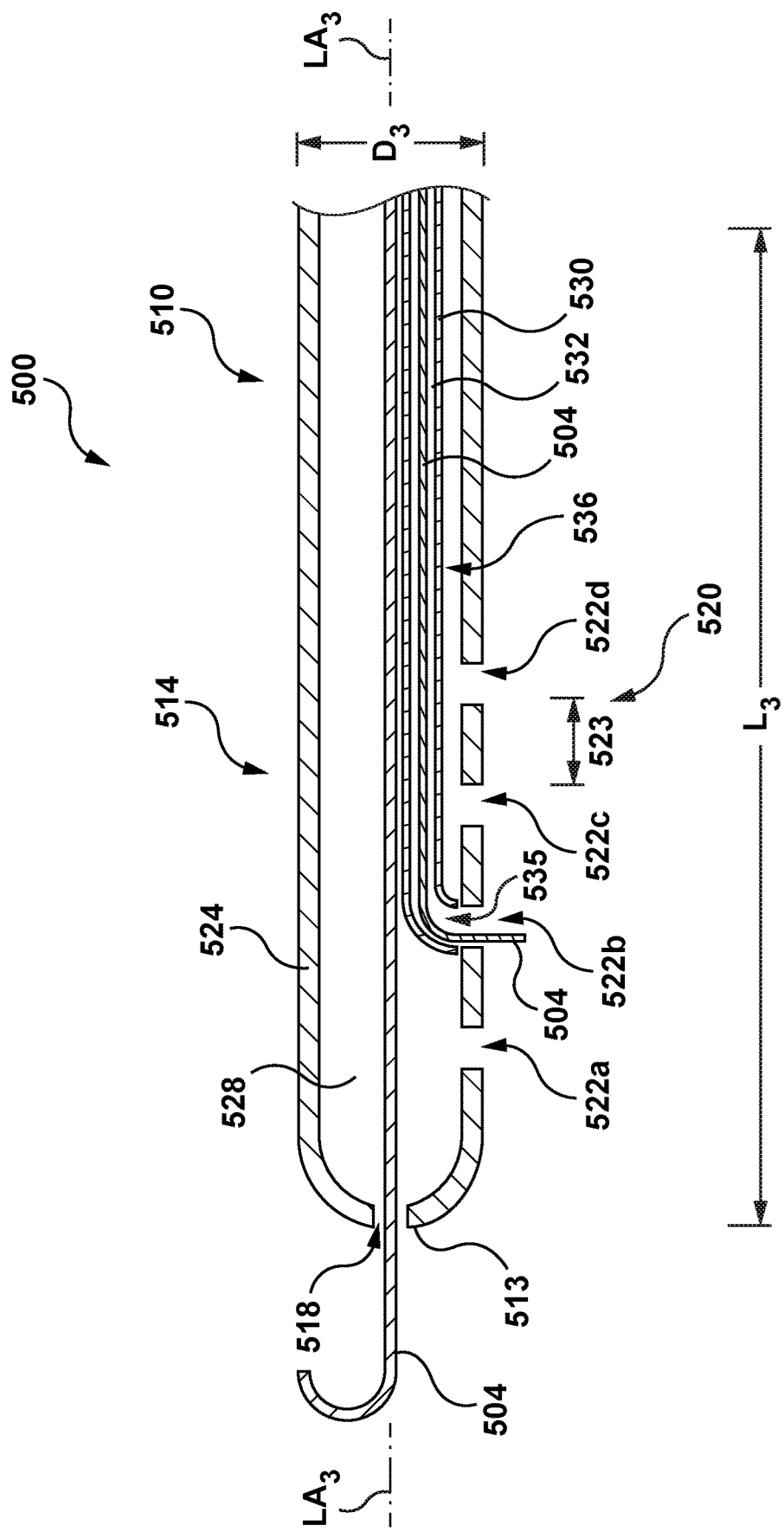

TRANSCATHETER GUIDEWIRE DELIVERY SYSTEMS, CATHETER ASSEMBLIES FOR GUIDEWIRE DELIVERY, AND METHODS FOR PERCUTANEOUS GUIDEWIRE DELIVERY ACROSS HEART VALVES

CROSS-REFERENCE TO RELATED APPLICATIONS

The present application is a divisional of U.S. patent application Ser. No. 15/253,377, filed Aug. 31, 2016, now allowed, the contents of which are incorporated by reference herein in their entirety.

FIELD OF THE INVENTION

The present technology relates generally to intravascular delivery of guidewires across a heart valve, catheter assemblies for guidewire delivery and associated methods. In particular, several embodiments are directed to catheter assemblies having alignment features for directing guidewires across heart valves, such as an aortic valve.

BACKGROUND OF THE INVENTION

The human heart is a four chambered, muscular organ that provides blood circulation through the body during a cardiac cycle. The four main chambers include the right atria and right ventricle which supplies the pulmonary circulation, and the left atria and left ventricle which supplies oxygenated blood received from the lungs to the remaining body. To insure that blood flows in one direction through the heart, atrioventricular valves (tricuspid and mitral valves) are present between the junctions of the atria and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber or structure (e.g., aorta) to occur at the proper flow rate and cause the heart to work harder to pump the blood through the diseased valve. Aortic stenosis, for example, can lead to chest pain, fainting, and heart failure. Valvular insufficiency or regurgitation occurs when the valve does not close completely, allowing blood to flow backwards, thereby causing the heart to be less efficient. For example, aortic valvular insufficiency results in blood pooling in the left ventricle which must then expand its normal capacity to accommodate the pooled volume of blood as well as the new blood received in the subsequent cardiac cycle. For this reason the heart muscle must work harder to pump the extra volume of blood which causes strain of the heart muscle over time as well as raises the blood pressure in the heart. A diseased or damaged valve, which can be congenital, age-related, drug-induced, or in some instances, caused by infection, can result in an enlarged, thickened heart that loses elasticity and efficiency. Other symptoms of heart valve diseases, such as stenosis and valvular insufficiency, can include weakness, shortness of breath, dizziness, fainting, palpitations, anemia and edema, and blood clots which can increase the likelihood of stroke or pulmonary embolism. Such symptoms can often be severe enough to be debilitating and/or life threatening.

Surgical strategies for repairing and/or replacing diseased or damaged heart valves can include percutaneously delivering interventional tools and/or prosthetic heart valve devices through catheter-based systems. Before delivering such tools and prosthetic devices, a guidewire may be used to introduce a delivery catheter and subsequently delivered prosthetic devices and/or tools into the proper position (e.g., within the aortic valve). For example, the delivery catheter may be introduced using a surgical cut down or Seldinger access to the femoral artery in the patient's groin. Once a guidewire is properly placed across the targeted heart valve, the delivery catheter may be introduced over the guidewire to the desired position using over-the-wire ("OTW") or rapid exchange ("RX") techniques. Spanning or crossing native heart valves, such as the aortic valve, with percutaneously placed guidewires can present numerous challenges due to differing anatomies and etiologies presented by individual patients. The varying shapes, sizes and other features associated with an abnormal or unhealthy aortic valve can make proper alignment of the guidewire difficult, especially in calcified valves which have a narrower opening during systole. In addition to being time consuming, such difficulties can result, in some instances, in cardiac tissue perforation by the guidewire, left bundle branch block and emboli dislodgement of calcium deposits at the aortic valve.

BRIEF SUMMARY OF THE INVENTION

Embodiments hereof are directed to catheter assemblies for delivering guidewires across a heart valve and methods for percutaneous guidewire delivery across heart valves, such as the aortic valve. The catheters and catheter assemblies have a compressed configuration for delivery via a vasculature or other body lumens to a native heart valve of a patient and have alignment features for stabilizing and aligning guidewires to be advanced across the targeted heart valves. In an embodiment, a catheter for crossing an aortic valve with a guidewire can include a tubular component having a proximal segment and a distal segment, wherein, in a deployed configuration, at least a portion of the distal segment has a loop configuration. The tubular component may also include a distal opening at a distal end of the distal segment, wherein the distal opening is configured to receive a guidewire therethrough, and include a proximal opening at a proximal end of the proximal segment, wherein the proximal opening is configured to receive a guidewire therethrough. The tubular component may further include a side port disposed along the distal segment proximal of the distal opening. In some arrangements, the distal segment, when in a delivery configuration, is conformable to a guidewire when the guidewire is disposed therein between the side port and distal opening. In one embodiment, retracting a guidewire proximal of the side port can cause the distal segment to transition between the delivery configuration and the deployed configuration. When in the deployed configuration, the side port can be in an open configuration such that a guidewire will exit the side port.

In another embodiment, a catheter apparatus may include an elongated tubular component having a proximal segment and a distal segment. The catheter apparatus may also include an alignment assembly having a loop shape in a distal portion of the distal segment of the elongated tubular component and which is adapted to be located at a target location adjacent a heart valve of a human patient. In certain arrangements, the elongated tubular component and the alignment assembly together define therethrough a guidewire lumen configured to slidably receive a medical guidewire, wherein axial movement of the guidewire relative to the alignment assembly can transform the alignment assembly between (a) a low-profile delivery configuration and (b) a deployed configuration tending to assume the loop shape of the alignment assembly. When in the deployed configuration, the alignment assembly can have a side port in an open configuration and positioned to allow a subsequent advancement of the guidewire to exit the side port in a non-axial direction relative to the guidewire lumen.

In yet another aspect, embodiments of the present technology provide a method of crossing an aortic valve with a guidewire. In one embodiment, the method can include advancing a catheter and a first guidewire through the vasculature of a patient to a location downstream of the aortic valve, wherein the first guidewire is disposed in a proximal segment and a distal segment of the catheter such that the catheter conforms to the shape of the first guidewire. The method may also include retracting the first guidewire proximal of the distal segment of the catheter, wherein retraction of the first guidewire can cause at least a portion of the distal segment of the catheter to deploy to a loop configuration to support the distal segment of the catheter against walls of a vessel adjacent to the aortic valve. The method may further include advancing a second guidewire distally such that the second guidewire exits a side port proximal of a distal end of the catheter, wherein the side port is faced towards the leaflets of the aortic valve to direct the second guidewire thereto.

In additional embodiments, a catheter assembly for crossing a heart valve with a guidewire may include a tubular support structure adapted to be located at a target location adjacent to the heart valve of a human patient. In certain embodiments, the support structure may include a proximal segment having a proximal opening at a proximal end, a distal segment having a distal opening at a distal end, and a plurality of spaced-apart side ports disposed proximal to the distal opening. The proximal segment and the distal segment together may define therethrough a guidewire lumen configured to slidably receive a first guidewire. The catheter assembly may also include a wire guide slidably disposed within the support structure. In various arrangements, the wire guide may have a lumen for slidably receiving a second guidewire through a proximal guidewire port disposed within a first portion and transmitting the second guidewire through a distal guidewire port disposed within a second portion. In one embodiment, axial movement of the wire guide relative to the support structure can align the distal guidewire port of the wire guide with one of the plurality of spaced-apart side ports, such that in a subsequent advancement of the second guidewire, the second guidewire can exit the aligned side port.

Additional aspects of the present technology may also be directed to catheter systems for aligning a therapeutic tool relative to an anatomical feature in a body lumen of a patient. In one embodiment, a system can include a tubular component and an alignment assembly disposed at a distal portion of the tubular component. The alignment assembly may be adapted to be located at a target location within the body lumen of the patient. Additionally, the alignment assembly can have an outer body and a lumen therethrough, and wherein the alignment assembly has a plurality of spaced-apart side ports. The system may also include a tool guide slidably disposed within the tubular structure and the alignment assembly. In some arrangements, the tool guide can have an internal lumen for providing a path for the therapeutic tool between a proximal opening and a distal opening. The system may further have an alignment guide disposed on an outer surface of the tool guide at a proximal portion adapted to remain outside the body of the patient. The alignment guide, in some embodiments, may provide a visual representation of the position of the distal opening relative to the plurality of spaced-apart side ports on the alignment assembly.

In a further aspect, embodiments of the present technology may provide another method of crossing an aortic valve with a guidewire. In one embodiment, the method can include advancing a support structure and a first guidewire through the vasculature of a patient to a location downstream of the aortic valve, wherein the first guidewire is disposed in a proximal segment and a distal segment of the support structure. The method may also include axially sliding a wire guide within the support structure such that a distal opening of the wire guide is axially aligned with one of a plurality of side ports disposed in the distal segment of the support structure. The method may further include advancing a second guidewire distally through the wire guide such that the second guidewire exits the aligned side port of the support structure towards the leaflets of the aortic valve.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

FIG. 9B is an enlarged sectional view of the distal segment of the catheter shown in FIG. 9A in accordance with an embodiment hereof.

DETAILED DESCRIPTION OF THE INVENTION

Specific embodiments of the present technology are now described with reference to the figures, wherein like reference numbers indicate identical or functionally similar elements. The terms "distal" and "proximal" are used in the following description with respect to a position or direction relative to the treating clinician or with respect to a catheter or catheter assembly. For example, "distal" or "distally" are a position distant from or in a direction away from the clinician when referring to delivery procedures or along a vasculature. Likewise, "proximal" and "proximally" are a position near or in a direction toward the clinician.

The following detailed description is merely exemplary in nature and is not intended to limit the present technology or the application and uses of the present technology. Although the description of embodiments hereof are in the context of treatment of heart valves and particularly in the context of gaining percutaneous access to an aortic valve, the present technology may also be used in any other body passageways where it is deemed useful. Furthermore, there is no intention to be bound by any expressed or implied theory presented in the preceding technical field, background, brief summary or the following detailed description.

Embodiments of the present technology as described herein can be combined in many ways to treat or access one or more of many valves of the body including valves of the heart such as the aortic valve. The embodiments of the present technology can be therapeutically combined with many known surgeries and procedures, for example, such embodiments can be combined with known methods of accessing the valves of the heart such as the aortic valve with retrograde approaches, antegrade approaches, and combinations thereof.

Figure 1:
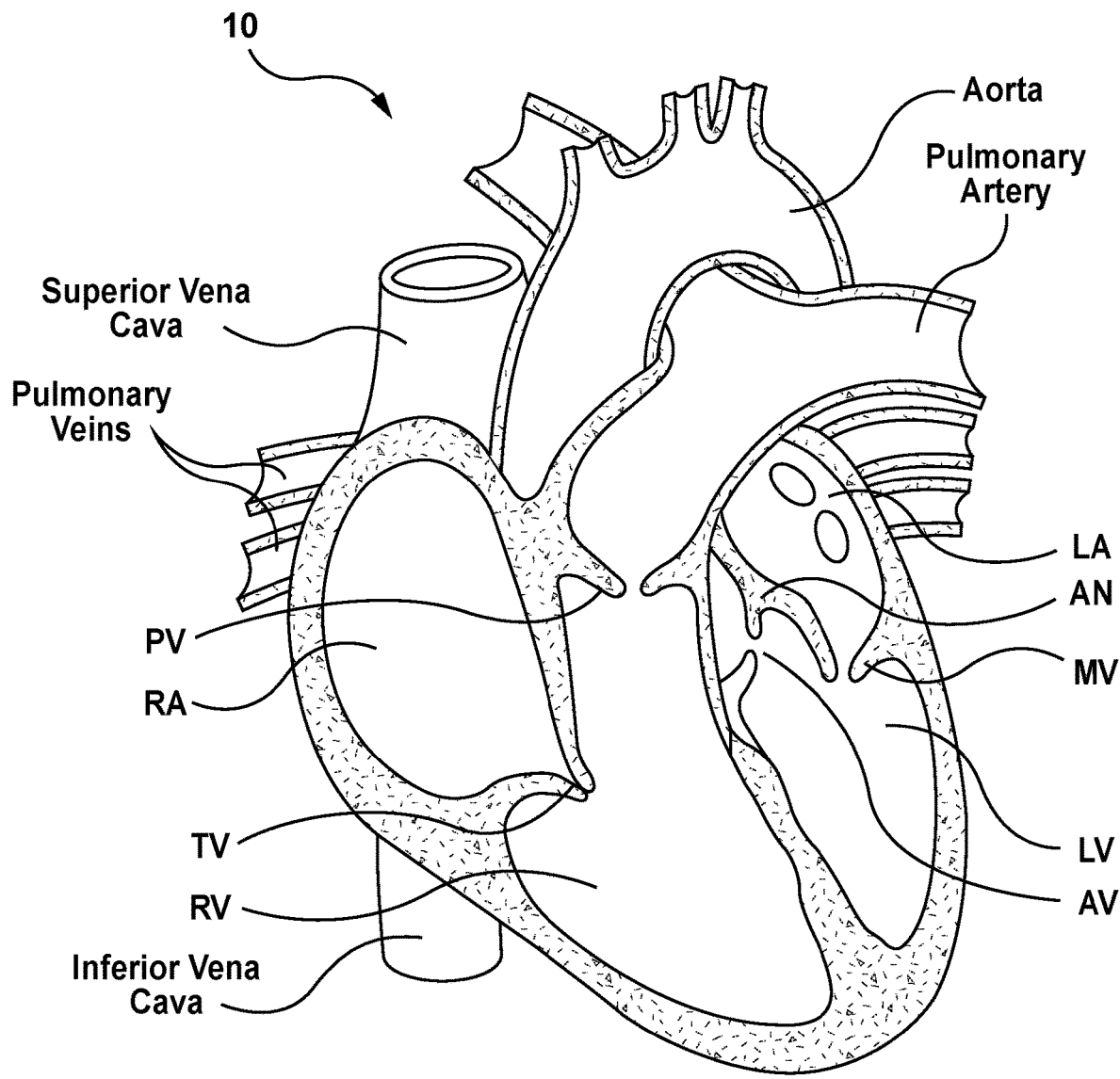
FIG. 1 is a schematic sectional illustration of a mammalian heart having native valve structures.
Figure 2B:
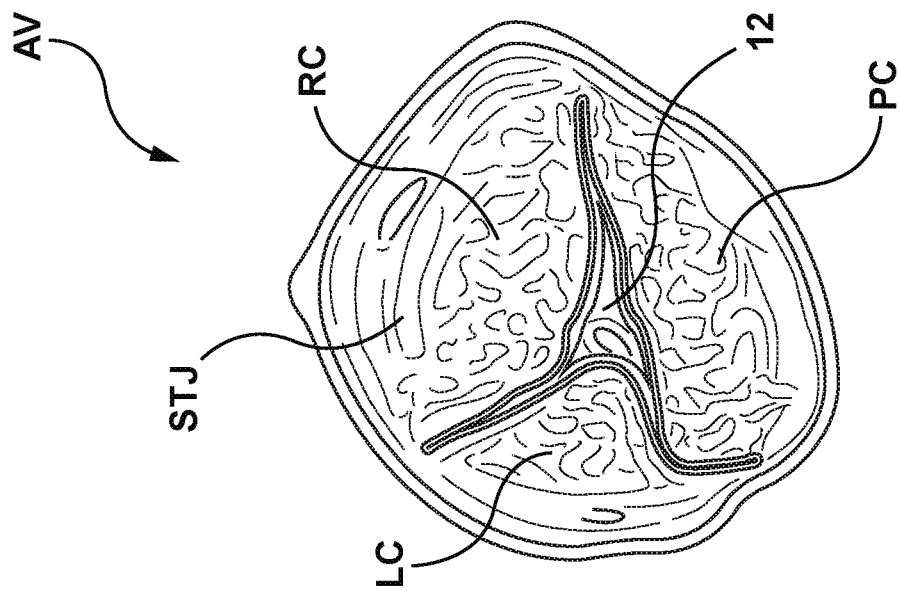
FIG. 2B is a schematic illustration of an inferior view of a stenotic or diseased aortic valve isolated from the surrounding heart structures and showing the annulus and native leaflets.
Figure 2A:
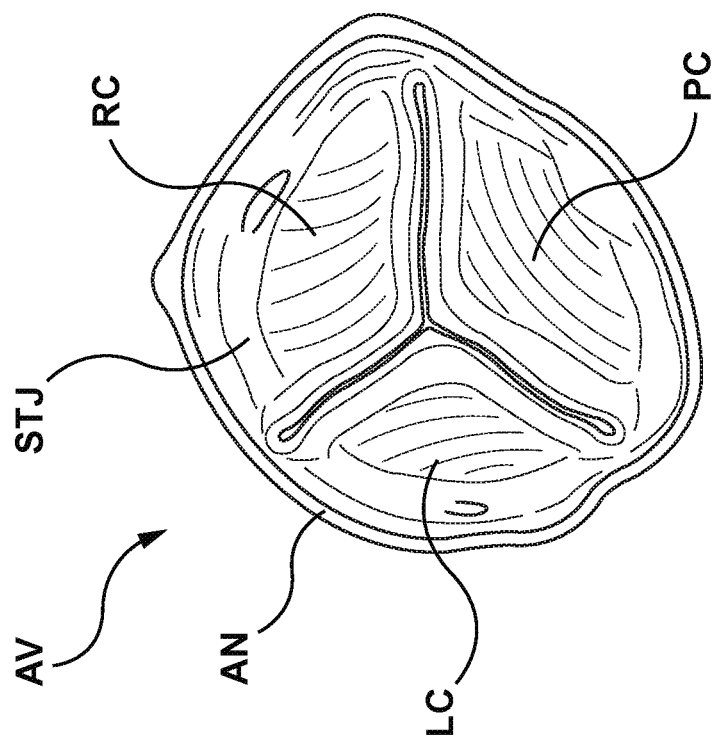
FIG. 2A is a schematic illustration of an inferior view of a healthy aortic valve isolated from the surrounding heart structures and showing the annulus and native leaflets.

FIG. 1 is a schematic sectional illustration of a mammalian heart 10 that depicts the four heart chambers (right atria RA, right ventricle RV, left atria LA, left ventricle LV) and native valve structures (tricuspid valve TV, mitral valve MV, pulmonary valve PV, aortic valve AV). FIG. 2A is a schematic illustration of an inferior view of a healthy aortic valve isolated from the surrounding heart structures and showing the annulus AN and native cusps or leaflets. Referring to FIGS. 1 and 2A together, the heart 10 comprises the left atrium LA that receives oxygenated blood from the lungs via the pulmonary veins. The left atrium LA pumps the oxygenated blood through the mitral valve MV and into the left ventricle LV during ventricular diastole. The left ventricle LV contracts during systole and blood flows outwardly through the aortic valve AV, into the aorta and to the remainder of the body.

In a healthy heart, the cusps (e.g., leaflets) of the aortic valve AV meet evenly at the free edges or "coapt" to close (FIG. 2A) and prevent back flow of blood from the aorta. Referring to FIG. 2A, the right cusp RC, the left cusp LC and the posterior cusp PC attach to the surrounding wall of the aorta at the sinotubular junction STJ above a fibrous ring of connective tissue called an annulus AN (FIG. 1). The flexible tissue of the aortic cusps (individually identified as RC, LC, and PC) open freely during left ventricle LV contraction to allow the blood to leave the heart chamber and be distributed systemically to the body's tissues. In a heart 10 having aortic valve stenosis, the aortic valve AV has narrowed causing the cusps (RC, LC, PC) to not sufficiently coapt or meet thereby forming a gap 12, as shown in FIG. 2B, that allows blood to back flow into the left ventricle LV. As such, aortic stenosis often results in a heart murmur that can be assessed by ultrasound. Typically, stenosis of the aortic valve AV prevents the valve from opening properly, forcing the heart muscle to work harder to pump blood through the valve. This can cause a pooling of blood and a pressure build-up in the left ventricle LV, which can thicken the heart muscle. One cause of valve stenosis includes progressive calcification of the valve (e.g., the aortic valve) which causes thickening and hardening of the tissue, and which can challenge crossing the valve with a guidewire for subsequent delivery of surgical tools and replacement prosthetic valves. Other causes of stenosis can include congenital defects (e.g., bicuspid valve), results of infections such as rheumatic fever or endocarditis, and age-related hardening of valve tissues.

Embodiments of catheter assemblies, delivery systems and associated methods in accordance with the present technology are described in this section with reference to FIGS. 3-14B. It will be appreciated that specific elements, substructures, uses, advantages, and/or other aspects of the embodiments described herein and with reference to FIGS. 3-14B can be suitably interchanged, substituted or otherwise configured with one another in accordance with additional embodiments of the present technology.

Provided herein are systems, devices and methods suitable for intravascular delivery of guidewires across a heart valve in a heart of a patient. In some embodiments, catheter assemblies and methods are presented for the treatment of valve disease as part of procedure steps for minimally invasive implantation of an artificial or prosthetic heart valve. For example, a catheter assembly, in accordance with embodiments described herein, can be used to direct and deliver a medical guidewire across a diseased or damaged native aortic valve or prior implanted prosthetic aortic valve in a patient, such as in a patient suffering from aortic valve stenosis illustrated in FIG. 2B. In further embodiments, the catheter assemblies and guidewire delivery systems disclosed herein are suitable for guidewire delivery across other diseased or damaged heart valves or prior implanted prosthetic heart valves, such as tricuspid, pulmonary and mitral heart valves.

Figure 3A:
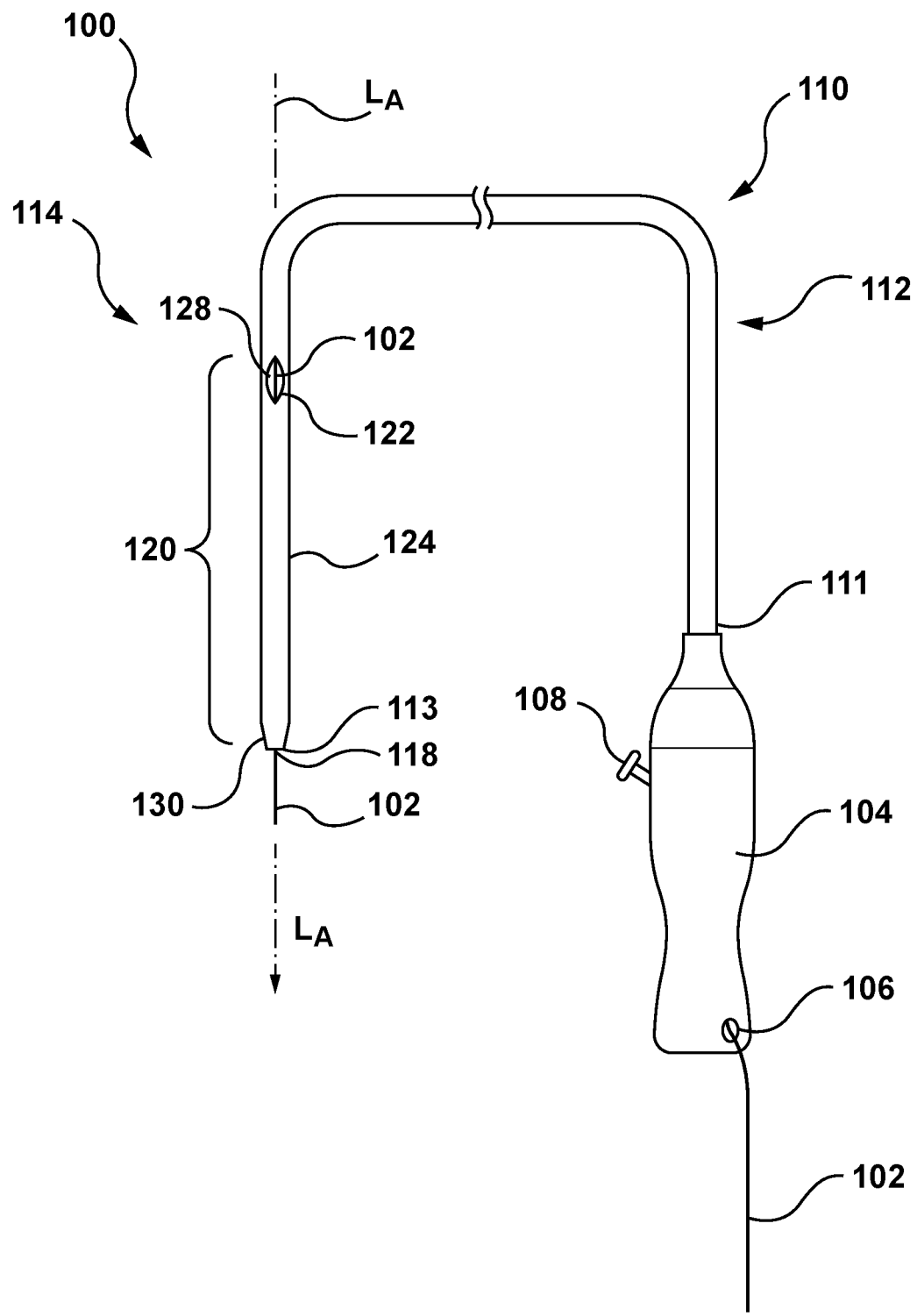
FIG. 3A is a side view of a minimally invasive catheter apparatus configured in accordance with an embodiment hereof.

FIG. 3A is a side view of a minimally invasive catheter apparatus 100 ("catheter 100") configured in accordance with an embodiment hereof. The catheter 100 may be used to align and deliver a medical guidewire 102 across a heart valve of a patient. As shown in FIG. 3A, the catheter 100 includes a handle 104 operatively coupled to an elongated tubular component 110 or shaft at a proximal end 111 of a proximal segment 112 of the tubular component 110. The catheter 100 further includes an alignment assembly 120 in a distal segment 114 of the tubular component 110 for directing a guidewire (e.g., guidewire 102) across a heart valve in a manner that aligns the guidewire with the coaptation region of the leaflets during systole. The tubular component 110 can have a generally hollow body that extends between the handle 104 at the proximal end 111 to the alignment assembly 120 in the distal segment 114. Together, the tubular component 110 and the alignment assembly 120 define therethrough a lumen 128 configured to slidably receive one or more guidewires (e.g., guidewire 102 or other guidewire) for delivering the alignment assembly 120 adjacent the heart valve and/or crossing the heart valve in an atraumatic manner. In the over-the-wire ("OTW") embodiment shown in FIG. 3A, a proximal end of the guidewire 102 extends from a handle port 106 in the handle 104.

As explained in further detail below, and in certain embodiments, the alignment assembly 120 can have a loop configuration (not shown) at least partially defined by an outer support structure 124, and at least one side port 122 disposed through the outer support structure 124 proximal of a distal end 113 of the alignment assembly 120, which can, in some embodiments, also be the distal end of the tubular component 110. In these embodiments, the alignment assembly 120 is configurable into a delivery state having a low-profile, or substantially straightened configuration for advancement of the alignment assembly 120 through the vasculature, for instance, to a target location adjacent an aortic valve of a patient. Upon delivery to the target location adjacent the aortic valve (e.g., downstream of the aortic valve), and at least partial retraction of the guidewire 102, the alignment assembly 120 is further configurable into a deployed state (not shown) having an expanded configuration (e.g., a loop-shaped configuration, a lasso-shaped configuration, a helical/spiral configuration) for engaging the internal walls of the aorta downstream of the aortic valve and/or at least partially resting on the cusps of the aortic valve (e.g., for stabilizing the alignment assembly 120). In the deployed state, the alignment assembly 120 provides a guidewire path through the side port 122 in a non-axial or transverse direction relative to the longitudinal or central axis $L_A$ of the lumen 128 of the tubular component 110. Further, the non-axial direction of the provided guidewire path can be adjusted to selectively align with a target region such as, for example, a region of leaflet coaptation of the aortic valve. Alternatively, the alignment assembly 120 may not assume a loop shape in the deployed state provided that the alignment assembly 120 is in another pre-shaped arrangement that provides a subsequently advanced guidewire an aligned path from the side port 122 across the aortic valve.

As explained in greater detail below, the alignment assembly 120 can be configured to be delivered intravascularly to a target heart valve (e.g., an aortic valve) of a human patient in the delivery state having a low-profile or substantially straightened configuration. Upon delivery to the target treatment site, the alignment assembly 120, in accordance with some embodiments, is further configured to be transformed into the deployed state having an expanded configuration (e.g., the distal portion of the tubular component 110 is expanded into a loop, lasso and/or spiral configuration). The alignment assembly 120 may be transformed between the delivery and deployed states using a variety of suitable mechanisms or techniques (e.g., self-expansion). In an embodiment, the alignment assembly 120 may be the distal segment 114 of the tubular component 110 that has a self-expanding tubular structure to transform into the deployed state when unrestricted (e.g., by retracting a guidewire, a guide catheter, straightening sheath, etc.). In another embodiment, the alignment assembly 120 may be a separate, self-expanding tubular structure coupled to the tubular component 110. In other embodiments, the alignment assembly 120 may be placed or transformed into the deployed state via remote actuation, e.g., via an actuator 108, such as a knob, pin, or lever carried by the handle 104. In other embodiments, however, the alignment assembly 120 may be transformed between the delivery and deployed states using other suitable mechanisms or techniques.

Figure 3B:
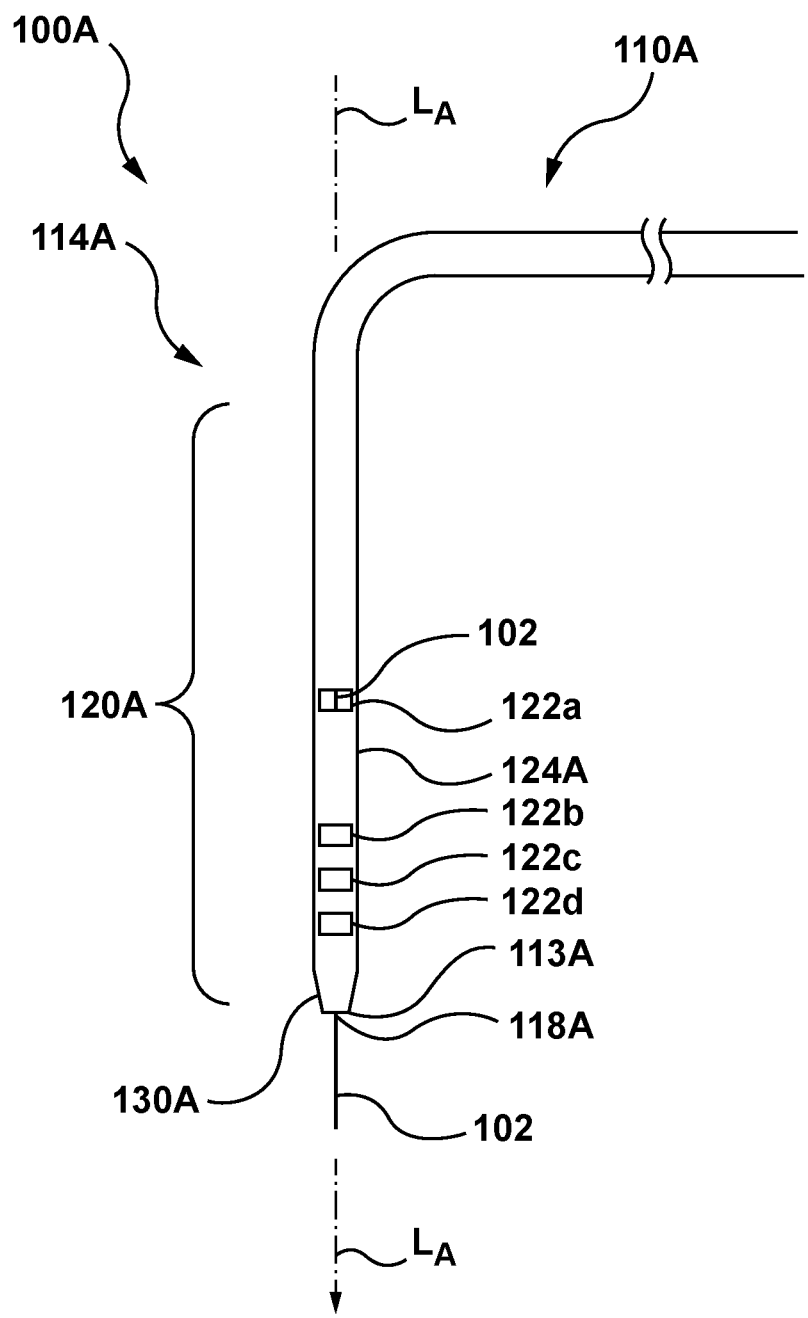
FIG. 3B is a partial side view of a minimally invasive catheter apparatus configured in accordance with another embodiment hereof.

FIG. 3B is a partial side view of a minimally invasive catheter 100A configured in accordance with another embodiment hereof. The catheter 100A includes several similar features to the catheter 100. For example, the catheter 100A includes an alignment assembly 120A in a distal segment 114A of an elongated tubular component 110A or hollow shaft for directing a guidewire (e.g., guidewire 102) across a heart valve in an atraumatic manner and/or in a manner that substantially aligns the guidewire with the coaptation region of the leaflets during systole. In the embodiment shown in FIG. 3B, the alignment assembly 120A includes an outer support structure 124A having a plurality of side ports 122a-122d spaced-apart along the distal segment 114A of the tubular component 110A. In these embodiments, the tubular component 110A and the alignment assembly 120A can define one or more lumens, such as lumens 328a, 328b as described below with reference to FIG. 7A, configured to receive a first guidewire (e.g., guidewire 102) therethrough for positioning the alignment assembly 120A at a target location adjacent an aortic valve of a patient. Upon delivery to the target location adjacent the aortic valve (e.g., downstream of the aortic valve), the alignment assembly 120A provides a guidewire path through a selected side port (e.g., any one of side ports 122a-122d) through which a subsequently advanced second guidewire (not shown) exits the selected side port in a non-axial or transverse direction relative to the longitudinal axis $L_A$ of the lumen (not shown) to cross the aortic valve.

Referring to FIGS. 3A and 3B together, the catheter 100, 100A may also include an atraumatic tip 130, 130A at the distal end 113, 113A of the tubular component 110, 110A and/or alignment assembly 120, 120A to prevent intravascular trauma during delivery of the alignment assembly 120, 120A to the aortic valve. The distal end 113, 113A of the alignment assembly 120, 120A and/or tubular component 110, 110A may also be configured to engage another element of the catheter 100, 100A. For example, the distal end 113, 113A of the alignment assembly 120, 120A may define a distal opening 118, 118A for receiving the guidewire 102 for delivery of the catheter 100, 100A using OTW or rapid exchange ("RX") techniques. In additional embodiments, the atraumatic tip 130, 130A or other features associated with the tubular component 110, 110A and/or alignment assembly 120, 120A (e.g., any one of side ports 122 or 122a-122d) can include radiopaque markers and/or be formed of radiopaque materials (e.g., barium sulfate, bismuth trioxide, bismuth subcarbonate, powdered tungsten, powdered tantalum, or various formulations of certain metals, including gold and platinum) that are capable of being fluoroscopically imaged to allow a clinician to determine if the alignment assembly 120, 120A is appropriately placed and/or deployed adjacent the aortic valve.

In several embodiments, the catheter 100 can be configured to allow locational adjustment of the direction and projected path a guidewire travels for crossing an aortic valve or other heart valve. For example, the catheter 100 can be pulled and pushed at a proximal segment 112 allowing fine control over the guidewire path as the guidewire exits a side port of the alignment assembly 120 (by example, the catheter 100 shown in FIG. 3A). In other embodiments (by example, the catheter 100A shown in FIG. 3B), a side port can be selected from a plurality of side ports 122a-122d such that a guidewire may traverse the side port and approach the valve structure in an atraumatic manner (e.g., without unintentional damage to the aortic valve). Accordingly, the catheters and methods described can also provide a physician or operator with improved control and placement of the guidewire during delivery across the aortic valve. Further details regarding such arrangements are described below with reference to FIGS. 4A-14B.

Following delivery and placement of a guidewire across a desired valve location, the catheter 100, 100A with alignment assembly 120, 120A and remaining guidewire (if any) can be removed from the heart and out of the body of the patient. Once percutaneous access is achieved, interventional tools, including a prosthetic heart valve, and supporting catheter(s) may be advanced to the heart intravascularly and positioned adjacent the target cardiac valve in a variety of manners, as described and known in the art. For example, once the guidewire is positioned, the endoluminal entry port is dilated to permit entry of a delivery catheter through the vasculature and along the guidewire path. In some instances, a protective sheath may be advanced to protect the vascular structure.

Selected Embodiments of Catheters Having Shape Set Loop Configurations

Figure 4A:
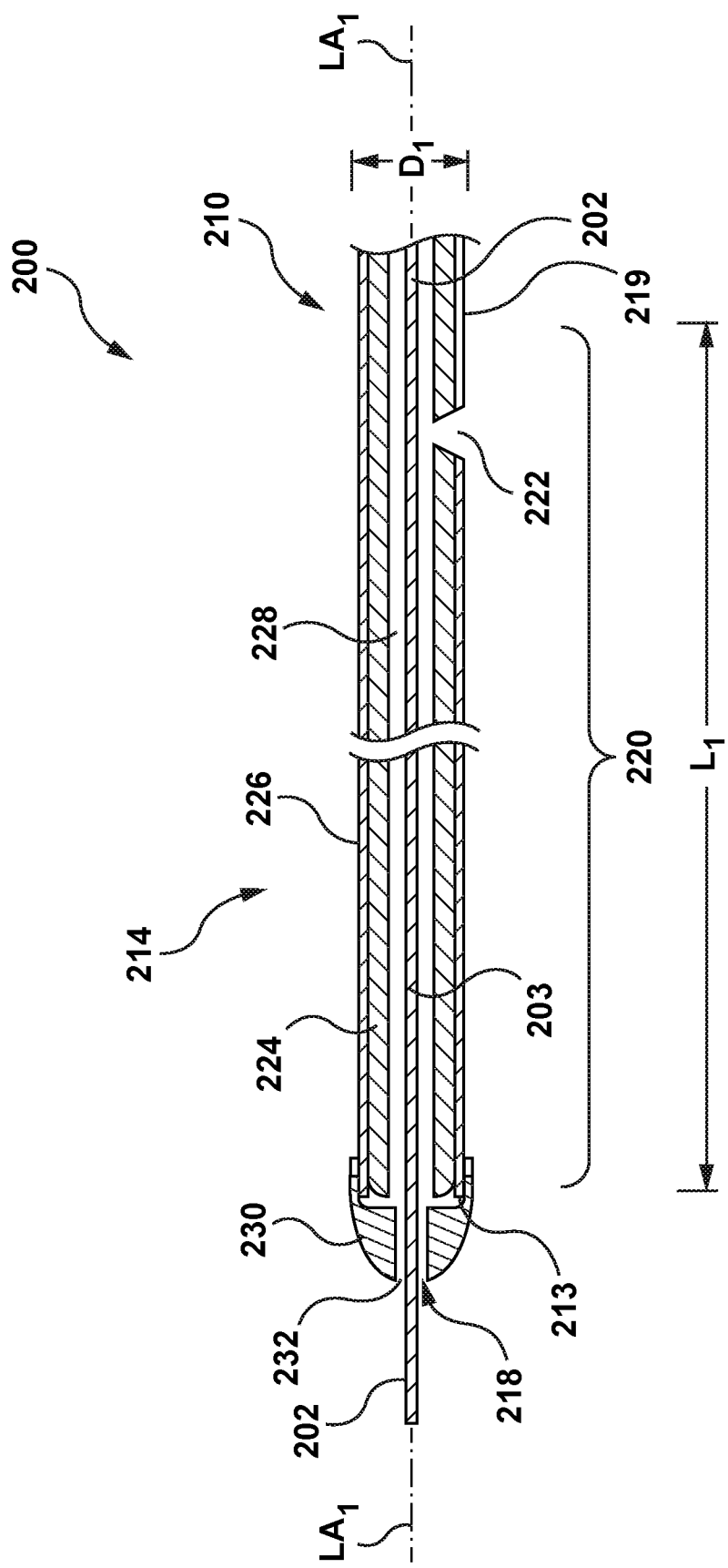
FIG. 4A is an enlarged sectional view of a distal segment of a catheter with an intravascular alignment assembly in a delivery state (e.g., low-profile or collapsed configuration) in accordance with an embodiment hereof.
Figure 4B:
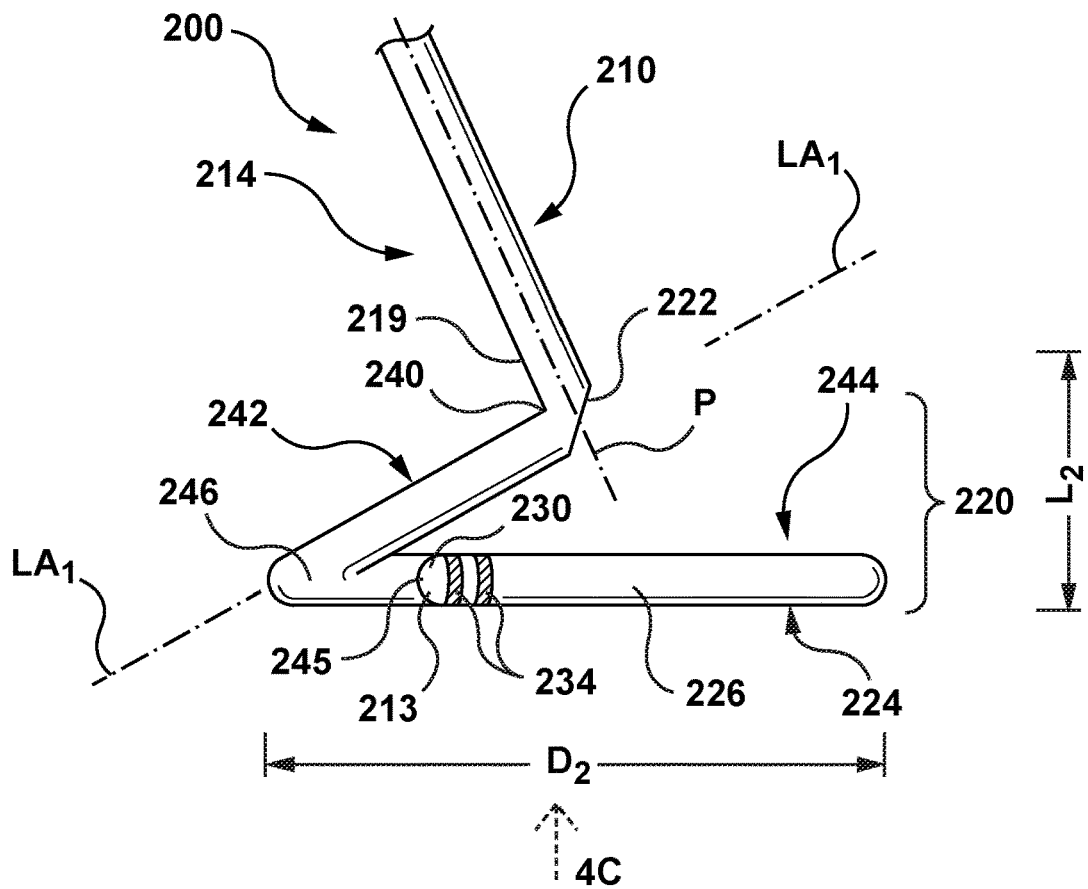
FIG. 4B is a side view of the distal segment of the catheter of FIG. 4A showing the alignment assembly in a deployed state (e.g., expanded configuration) in accordance with an embodiment hereof.

FIG. 4A is an enlarged, longitudinal cross-sectional view of a distal segment 214 of an elongated shaft or tubular component 210 of a catheter 200 having an intravascular alignment assembly 220 in a delivery state (e.g., a low-profile, substantially straightened or collapsed configuration) and in accordance with an embodiment of the present technology, and FIG. 4B is a side view of the distal segment 214 showing the alignment assembly 220 of FIG. 4A in a deployed state (e.g., an expanded configuration). As noted for some of the embodiments of the alignment assemblies 120 discussed above (FIG. 3), the alignment assembly 220 can be transformed or actuated between the delivery state (FIG. 4A) and the deployed state (e.g., a loop, lasso, coil and/or helical/spiral configuration, FIG. 4B).

Referring to FIGS. 4A and 4B together, the alignment assembly 220 includes an alignment member 224 that has been shape-set to have a loop configuration (FIG. 4B), and a side port 222 disposed proximal to a distal end 213 of the alignment assembly 220, or stated another way disposed distal to a proximal end 219 of the alignment assembly 220. Optionally, the alignment member 224 can be at least partially surrounded by a covering 226, such as a sleeve or other coating. The alignment assembly 220 can define a tubular structure having a low-profile outer dimension $D_1$ (e.g., circular or non-circular dimension), a longitudinal axis $LA_1$, and a lumen 228 for slidably receiving a guidewire 202 during delivery or removal of the alignment assembly 220 (FIG. 4A). As described further below, the lumen 228 is disposed through the alignment member 224 and the side port 222 spans the covering 226, if present, and the alignment member 224 to provide a guidewire exit path P from the lumen 228 to outside of the alignment assembly 220 when the alignment member 224 is deployed to the loop configuration (FIG. 4B). In the delivery or substantially straightened state, the side port 222 is in a closed configuration such that the guidewire 202 is aligned with the longitudinal axis $LA_1$ of the alignment assembly 220 (FIG. 4A); however, in the deployed state, for example, the side port 222 is in an open configuration such that the guidewire 202 follows the path P, which is aligned with the side port 222, such that the guidewire 202 exits the alignment assembly 220 in a non-axial or non-parallel direction to the longitudinal axis $LA_1$ at the distal segment 214 (FIG. 4B).

Referring to FIG. 4A, one embodiment of the alignment assembly 220 may be restrained in the delivery state (e.g., a generally straight or collapsed configuration) with the guidewire 202 disposed within the lumen 228 of the alignment assembly 220. The guidewire 202 may be sufficiently stiff to keep the alignment member 224 relatively straight and the side port 222 in a closed configuration in the delivery state. In this embodiment, the alignment member 224 conforms to the general shape of the guidewire 202 during delivery of the catheter 200 through the vasculature. It will be understood that, without additional bending stiffness provided by either the guidewire 202 or another delivery element (e.g., straightening sheath, guide catheter, etc.), the alignment assembly 220 will tend to return to the pre-formed shape of the alignment member 224 (e.g., loop shape, lasso shape, etc.) as shown in FIG. 4B. When the guidewire 202 is partially retracted or withdrawn from at least the distalmost region of the alignment assembly 220 (e.g., proximal to the side port 222), as illustrated in FIG. 4B, the alignment member 224 provides a shape-recovery force sufficient to overcome the straightening force provided by a distalmost portion 203 of the guidewire 202 such that the alignment assembly 220 can deploy into its loop-shaped (or, alternatively, lasso-shaped, helical/spiral-shaped) configuration with the side port 222 in the open configuration. Further, because the distalmost portion 203 of the guidewire 202 can remain at least partially within the alignment assembly 220 while in the deployed state (by way of example, the deployed state shown in FIG. 4B), the guidewire 202 can impart additional structural integrity to the positioning of the loop-shaped portion prior to subsequent guidewire 202 advancement through the side port 222 and toward the aortic valve leaflets. The columnar strength imparted by the guidewire 202 is expected to help mitigate or reduce problems associated with keeping the alignment assembly 220 in place through the cardiac cycle (e.g., systolic blood flow through the aorta).

In an alternate method step, the guidewire 202, including the distalmost portion 203, may be withdrawn completely from the alignment assembly 220 while remaining within the tubular component 210 to permit the transformation of the alignment assembly 220. In yet another method step, the guidewire 202 may be withdrawn completely from the shaft 210. In any of the foregoing examples, the clinician can withdraw the guidewire 202 sufficiently to observe transformation of the alignment assembly 220 to the deployed configuration and/or until an X-ray image shows that the distalmost portion 203 of the guidewire 202 is at a desired location relative to the alignment assembly 220 (e.g., at least partially withdrawn from the alignment assembly 220, or completely withdrawn from the alignment assembly 220, etc.). In some methods, the extent of withdrawal of the guidewire 202 can be based, at least in part, on the clinician's judgment with respect to the selected guidewire and the extent of withdrawal necessary to achieve deployment of the alignment assembly 220. In various arrangements, once the alignment assembly 220 has assumed the deployed state, the guidewire 202 can be subsequently advanced within the alignment assembly 220 to exit the side port 222 in the non-axial direction and in the direction of the aortic valve. In some embodiments, the guidewire 202 can be completely withdrawn from the catheter 200 and a second guidewire (not shown) can be subsequently advanced through the tubular component 210 and the lumen 228 of the alignment assembly 220 to exit the side port 222 when in the deployed state. For example, in one embodiment, a J-tip guidewire can be used to advance the catheter 200 having the alignment assembly 220 through the vasculature, and a straight-tip guidewire can be subsequently advanced following deployment of the alignment assembly 220 to cross the aortic valve.

In one embodiment, the side port 222 can be a slit, skive, slice or other hole formed in the components of the alignment assembly 220 on one side of the tubular component 210 and may form a joint and/or a weak region (e.g., on an opposite side of the tubular component 210) at which the tubular component 210 naturally bends. For example, the side port 222 can be formed by removing a slice or skive from the covering 226 and the alignment member 224 during manufacturing. In other embodiments, the side port 222 can be formed by puncturing a hole or inserting an eyelet or other feature to form an opening through which a guidewire can advance. In the delivery state, the side port 222 can be in a closed or otherwise inaccessible configuration such that a guidewire 202 advanced through the lumen 228 of the tubular component 210 would advance along a first guidewire path that continues within the lumen 228 to a distal opening 218 at the distal end 213 of the alignment assembly 220 (FIG. 4A). When deployed, the side port 222 is positioned along the tubular component 210 in a location proximal of the loop configuration (FIG. 4B). In operation, a subsequently advanced guidewire 202 would advance along a second guidewire path that ends at a bend 240 in the tubular component 210 at or near the side port 222. The portion of the lumen 228 proximal to the bend 240 remains uncompromised and a guidewire 202 traveling therethrough would exit the side port 222 adjacent the bend 240 (FIG. 4B). In other embodiments, the bend 240 can be a feature of the alignment member 224 that is set during the manufacturing process. In such embodiments, a punctured hole (not shown) or other added feature (e.g., eyelet) can be positioned in alignment with a portion of the lumen 228 proximal of the side port 222 when the alignment assembly 220 is in the deployed state (FIG. 4B).

Figure 4C:
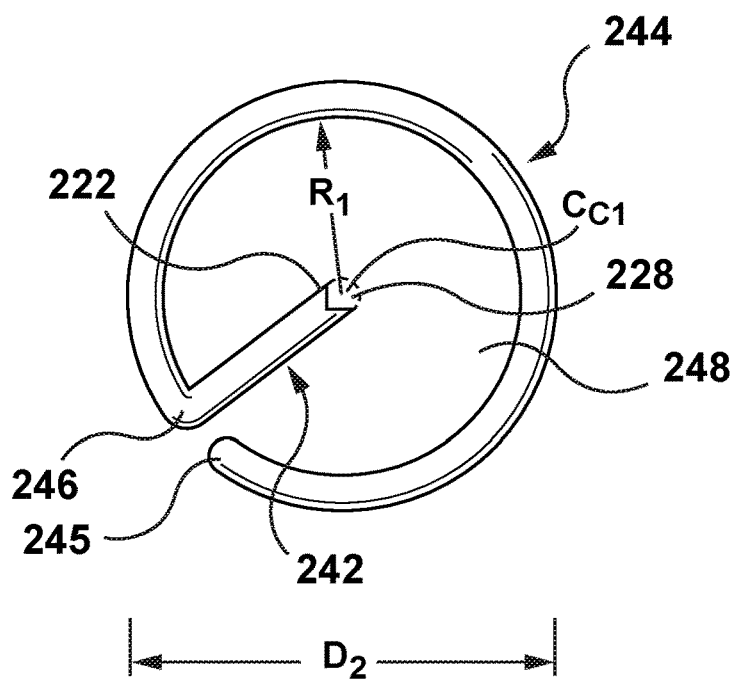
FIG. 4C is a transverse end view of the alignment assembly shown in the direction of the arrow 4C of FIG. 4B.

The pre-formed, loop-shaped configuration of the alignment assembly 220 is further illustrated in FIG. 4C, which is a transverse end view of the alignment assembly 220 in the direction of the arrow 4C of FIG. 4B. Referring to FIGS. 4B and 4C together, the distal region of the alignment assembly 220 defines a loop or circular shape in a direction radially outward from a center of curvature $C_{C1}$, and that self-expands to a deployed geometry within the aorta A (described further below with reference to FIG. 4D). As further illustrated in FIGS. 4B and 4C, transitioning from the bend 240, in the loop configuration, the alignment assembly 220 defines or possesses a longitudinal segment 242 followed by circumferential segment 244, which forms the loop shape about the center of curvature $C_{C1}$. The longitudinal segment 242 extends distally and radially, i.e., is angled, from the bend 240 for positioning an origin 246 of the circumferential segment 244 in contact with or very close to a wall, annulus or other anatomy of the region, as described below. In the illustrated embodiment, the distal end 213 of the alignment assembly 220 is also a terminal end 245 of the circumferential segment 244. Referring to FIG. 4C, the terminal end 245 of the circumferential segment 244 substantially meets and/or is aligned with the origin 246 of the circumferential segment 244 creating a single loop having a radius $R_1$. In alternative arrangements, not shown, the terminal end 245 may not meet the origin 246, such as for example if the loop formed a coil (e.g., wherein the terminal end 245 overlaps with the origin 246). In still other arrangements, the circumferential segment 244 may not complete an entire loop such that there is a gap (wider opening) between the terminal end 245 and the origin 246.

In some embodiments, the radius $R_1$ of the loop shape formed by the circumferential segment 244 is sized greater than a radius of an aortic valve AV such that portions of the circumferential segment 244 can at least partially rest on an annulus of the aortic valve, and/or engage an inner wall of the aorta. In other embodiments, the radius $R_1$ is less than a radius of an aortic valve such that portions of the circumferential segment 244 can at least partially rest on cusps of the aortic valve. Additionally, the size of the loop shape (e.g., the radius $R_1$) may be selected to engage the aorta, a subannular region of the aortic valve and/or other anatomical features of the patient's anatomy without blocking or inhibiting a guidewire 202 from crossing the native valve, or stated another way to allow the guidewire 202 to pass through a central space 248 that is created or defined by the loop shape (FIG. 4C) as the guidewire is maneuvered for crossing the native valve.

As mentioned above, the alignment member 224 may be used to impart a loop shape to the alignment assembly 220. In one embodiment, the alignment member 224 can be a tubular structure comprising a nickel titanium alloy (e.g., nitinol) multi-filar stranded wire with a lumen therethrough, such as, for example, as sold under the trademark HELICAL HOLLOW STRAND (HHS), and commercially available from Fort Wayne Metals of Fort Wayne, Ind. The alignment member 224 may be formed from a variety of different types of materials, may be arranged in a single or dual-layer configuration, and may be manufactured with a selected tension, compression, torque, pitch direction, or other characteristics. The HHS material, for example, may be cut using a laser, electrical discharge machining (EDM), electrochemical grinding (ECG), or other suitable means to achieve a desired finished component length and geometry.

Forming the alignment member 224 of nitinol multi-filar stranded wire(s) or other similar materials is expected to provide a desired level of support and rigidity to the alignment assembly 220 without additional reinforcement wire(s) or other reinforcement features within the alignment assembly 220. In one embodiment, the looped shape structure can be formed from a shape memory material (e.g., nitinol) wire or tube that is shaped around a mandrel (not shown) using conventional shape-setting techniques known in the art. In one specific example, nitinol shape memory wire can typically be heated to approximately 510° C. for approximately 5 minutes followed by a water quench. In another embodiment, a flat sheet of nitinol or other shape memory material can be fabricated and further wrapped about a shape rod or mandrel for pre-forming the loop shape of the alignment member 224. A desired stiffness of the alignment member 224 and/or alignment assembly 220 can be provided using variations in a braid or weave pattern, coiled structures, woven structures and/or wire density as known by one of ordinary skill in the art of fabricating shaped devices. In one embodiment, the stiffness of the alignment member 224 can vary along a length of the alignment member 224 such as, for example, regions at or near the side port 222 may have a greater stiffness than regions comprising the circumferential segment 244. In various embodiments, the stiffness of the guidewire 202 used to deliver the alignment assembly 220 to the target region at near the aortic valve AV may be greater than a stiffness of the alignment member 224 such that the alignment assembly 220 can be more easily tracked through the vasculature during delivery.

In one embodiment, the covering 226 provides a sleeve or pre-applied coating over the alignment member 224 to isolate the material (e.g., nitinol) of the alignment member 224 (e.g., as shown in FIG. 4A) from the vasculature. The covering 226 may be composed of a polymer material such as polyamide, polyimide, polyether block amide copolymer sold under the trademark PEBAX, polyethylene terephthalate (PET), polypropylene, an aliphatic, polycarbonate-based thermoplastic polyurethane sold under the trademark CARBOTHANE, or a polyether ether ketone (PEEK) polymer or other suitable materials. The material properties and dimensions of the covering 226 are selected to provide the necessary flexibility for the covering 226 to readily deform between a relaxed, substantially straight shape and the loop shape configuration of the alignment member 224 in the deployed state. In other words, the covering 226 is more flexible than the alignment member 224 such that the shape of the combined components is defined in large part by the shape of the alignment member 224.

In one embodiment, the alignment member 224 and inner wall of the covering 226 can be in intimate contact with little or no space between the alignment member 224 and the covering 226 (as best seen in FIG. 4A). In some embodiments, for example, the covering 226 can have a larger cross-sectional dimension (e.g., diameter) than the alignment member 224 before assembly such that applying hot air to the covering 226 during the manufacturing process shrinks the covering onto the alignment member 224, as will be understood by those familiar with the ordinary use of shrink tubing materials. This feature is expected to inhibit or eliminate wrinkles or kinks that might occur in the covering 226 as the alignment assembly 220 transforms from the relatively straight delivery state (FIG. 4A) to the generally loop-shaped configuration in the deployed state (e.g., FIG. 4B).

In other embodiments, the alignment member 224 and/or other components of the alignment assembly 220 may be composed of different materials and/or have a different arrangement. For example, the alignment member 224 may be formed from other suitable shape memory materials (e.g., wire or tubing besides HHS or nitinol, shape memory polymers, electro-active polymers) that are pre-formed or pre-shaped into the desired deployed state. Alternatively, the alignment member 224 may be formed from multiple materials such as a composite of one or more polymers and metals.

In some embodiments, the alignment assembly 220 terminates at an atraumatic tip 230 (FIGS. 4A and 4B). The atraumatic tip 230 can be a flexible curved or tapered tip. In one embodiment, the atraumatic tip 230 may have a distal opening 232 for accommodating the guidewire 202 when the alignment assembly 220 is in the delivery state (FIG. 4A). The curvature of the atraumatic tip 230 can be varied depending upon the particular sizing/configuration of the alignment assembly 220. In some embodiments, the atraumatic tip 230 may also comprise one or more radiopaque markers 234 (FIG. 4B) and/or one or more sensors (not shown). In one embodiment, the atraumatic tip 230 can be part of the tubular component 210 and/or the alignment assembly 220 (e.g., an extension of or integral with the alignment assembly 220 and/or alignment member 224). In one example, the atraumatic tip 230 can be a more flexible tapered portion (e.g., about 5 to about 7 mm) of the distal end of the alignment member 224. Such an arrangement can be suitable for guidewire delivery of the alignment assembly 220 to the target location adjacent the aortic valve. In another embodiment, the atraumatic tip 230 can be a separate component that may be affixed to the distal end 213 (FIG. 4A) of the tubular component 210 and/or alignment assembly 220 via adhesive, crimping, over-molding, or other suitable techniques. The atraumatic tip 230 can be made from a polymer material (e.g., a polyether block amide copolymer sold under the trademark PEBAX, or a thermoplastic polyether urethane material sold under the trademarks ELASTHANE or PELLETHANE), or other suitable materials having the desired properties, including a selected durometer. In other embodiments, the atraumatic tip 230 may be formed from different material(s) and/or have a different arrangement.

Figure 4D:
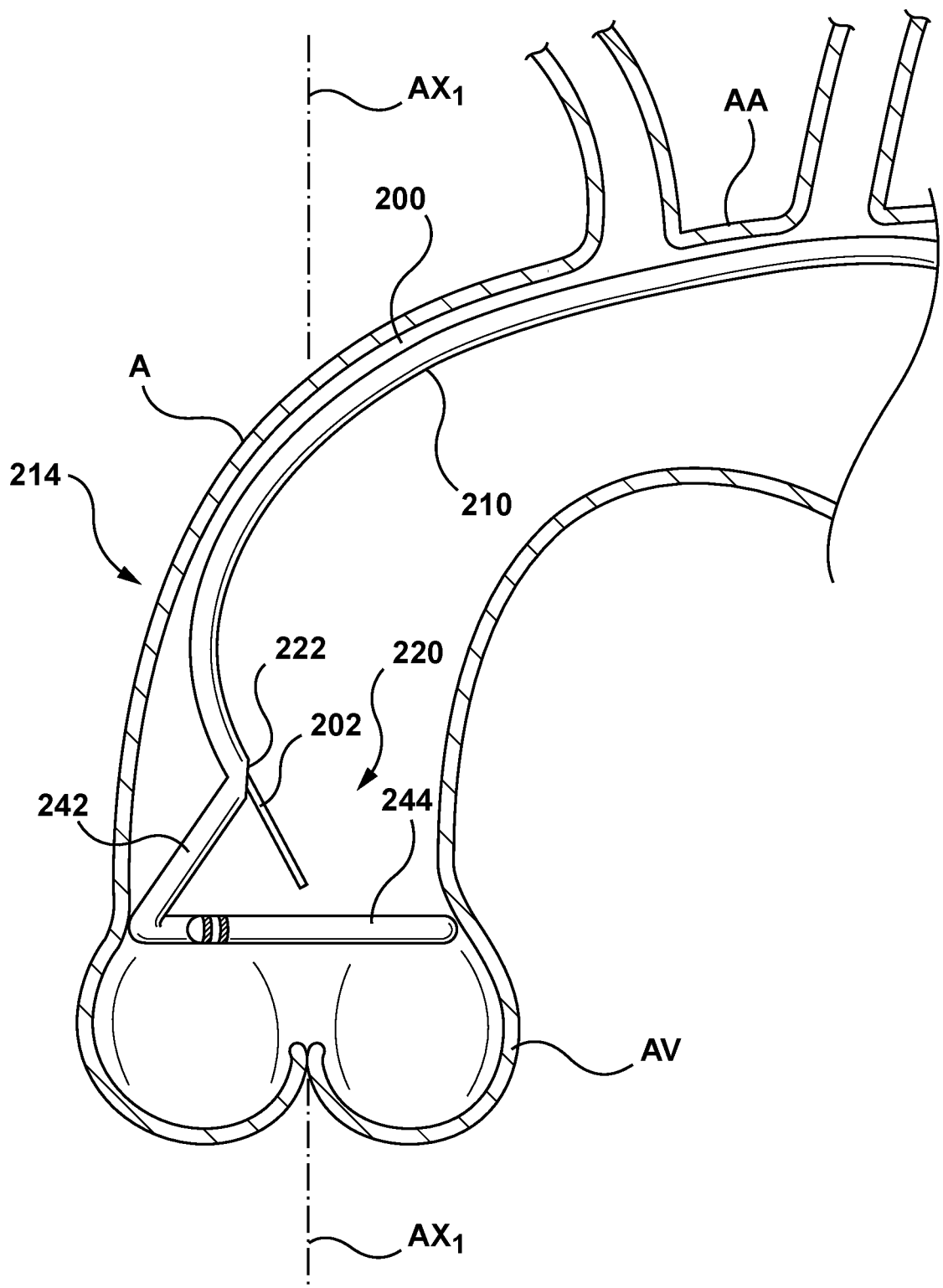
FIG. 4D illustrates a cut-away view of an aorta and aortic valve of a patient and showing a partial side view of the intravascular alignment assembly of FIGS. 4A-4C having a loop-shaped configuration in a deployed state (e.g., expanded configuration) in accordance with a further embodiment hereof.

FIG. 4D illustrates a cut-away view of an aorta A and aortic valve AV of a patient and showing a partial side view of the intravascular alignment assembly 220 of FIGS. 4A-4C having a loop-shaped configuration in a deployed state (e.g., expanded configuration) in accordance with a further embodiment of the present technology. As noted above, the alignment assembly 220 can be transformed or actuated between the delivery state (FIG. 4A) and the deployed state (e.g., having a radially expanded, loop-shaped configuration, FIGS. 4B-4D), such as following delivery of the alignment assembly 220 to the target location downstream of the aortic valve AV. In one embodiment, the portions of the alignment member 224 that are configured to assume the loop configuration can be transformed when the guidewire 202 (FIG. 4A), for example, is pulled proximally while the alignment assembly 220 is held stationary relative to the target location. Alternatively, the alignment assembly 220 can be pushed distally beyond the distalmost portion 203 of the guidewire 202 while the guidewire 202 is held stationary relative to the target location.

The side port 222 as depicted in FIGS. 4B and 4C is also shown in the open configuration in FIG. 4D. As best seen in FIGS. 4C and 4D, the side port 222 is oriented toward the central space 248 created by the circumferential segment 244 of the pre-formed loop configuration. In operation, an advancement of the guidewire 202 from the lumen 228 (FIG. 4A) through the side port 222 will cross a plane of the pre-formed loop configuration through the central space 248 (FIG. 4C) and continue toward the aortic valve (FIG. 4D).

Referring back to FIG. 4A, in the delivery state the alignment assembly 220 has an outer diameter or dimension $D_1$ that is sized to provide a low profile thereto, and an axial length $L_1$ between the proximal and distal ends 219, 213 thereof. As shown in FIG. 4B, in the radially-expanded state the alignment assembly 220 achieves a loop-shaped configuration that is characterized, at least in part, by an outer diameter or dimension $D_2$ and axial length $L_2$ between the proximal and distal ends 219, 213 thereof. In particular, the expanded loop-shaped configuration of the alignment assembly 220 may be characterized by its axial length $L_2$ along the axis of elongation in free space, e.g., not restricted by a vessel wall or other structure. As the alignment assembly 220 radially expands from its delivery state, its low-profile outer dimension $D_1$ (FIG. 4A) increases to its radially-expanded outer dimension $D_2$ (FIGS. 4B and 4C) and its axial length decreases. That is, when the alignment assembly 220 deploys into the loop shape configuration, the distal end 213 of the alignment assembly 220 moves axially towards the proximal end 219 of the alignment assembly 220 (or vice versa). Accordingly, the deployed axial length $L_2$ is less than the unexpanded or delivery axial length $L_1$. As such, subsequent to deployment within the aorta A (FIG. 4D), the orientation and/or position of the deployed loop-shaped configuration within the aorta A may need to be adjusted relative to the aortic valve AV. For example, in one embodiment, the deployed alignment assembly 220 may need to be moved further downstream toward the aortic valve AV following deployment (e.g., if the distal end 213 moves axially toward the proximal end 219 during deployment). Movement of the deployed alignment assembly 220 within the aorta A can be accomplished, for example, by pushing the proximal segment (not shown) of the catheter 200 from outside of the body in a distal direction (e.g., until the loop configuration is in a desired location relative to the aortic valve AV).

As shown in FIG. 4D, the loop-shaped configuration has the circumferential segment 244 that expands in a direction toward the inner wall of the aorta A such that at least portions of the circumferential segment 244 engage the inner wall. Referring back to FIG. 4C, the circumferential segment 244 can be generally circular when in an unbiased configuration (e.g., when radial expansion of the expanded configuration is not limited by an opposing structure); however, in other embodiments, other shapes are possible (e.g., oval, irregular etc.). When deployed within the aorta A or other structure in the body, at least portions of the circumferential segment 244 can be biased, for example, in a direction radially inward toward the center of curvature $C_{C1}$ to accommodate the shape of the surrounding anatomical features. With reference to FIGS. 4C and 4D together, and upon deployment within the aorta A of the patient, an axis line (not shown) drawn through the center of curvature $C_{C1}$ of the circumferential segment 244 is substantially aligned with (e.g., is substantially coincident with) a central axis $A_{X1}$ of the ascending aorta A in a manner that positions the circumferential segment 244 in contact with the inner wall of the aorta A (or other anatomical structure) while generally positioning the side port 222 in alignment with a center (e.g., leaflet coaptation region) of the aortic valve AV. In other arrangements, the size, shape and orientation of the inner wall of the aorta A causes the axis line through the center of curvature $C_{C1}$ to be misaligned with a center and/or leaflet coaptation region of the aortic valve AV. In these instances, the clinician can adjust the guidewire path exiting the side port 222 such that the guidewire path crosses the center and/or leaflet coaptation region of the aortic valve as discussed further herein.

Figure 5C:
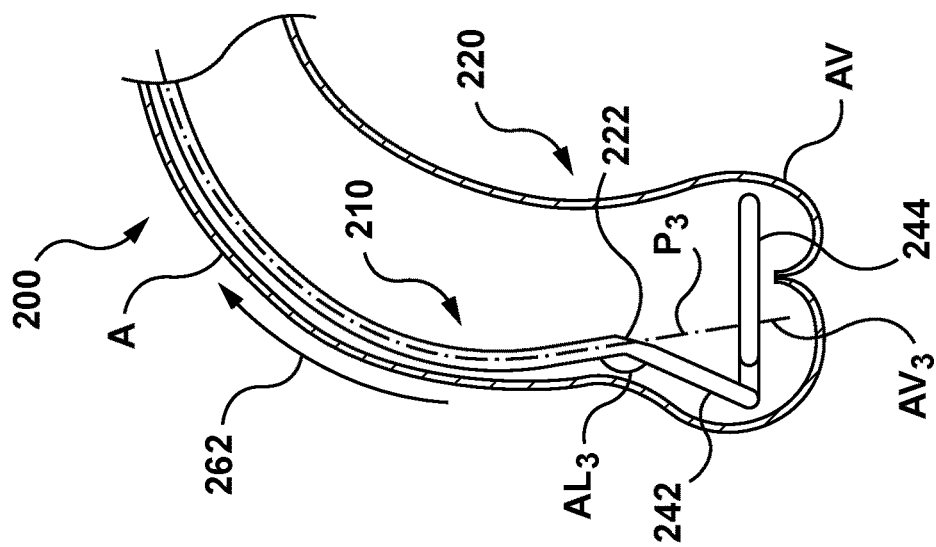
FIGS. 5A-5C are partial side views of the catheter of FIGS. 4A-4D showing the alignment assembly deployed within the aorta A of a patient and illustrating steps in a method for adjusting a guidewire path through a loop shape thereof and across the aortic valve in accordance with an embodiment hereof.
Figure 5B:
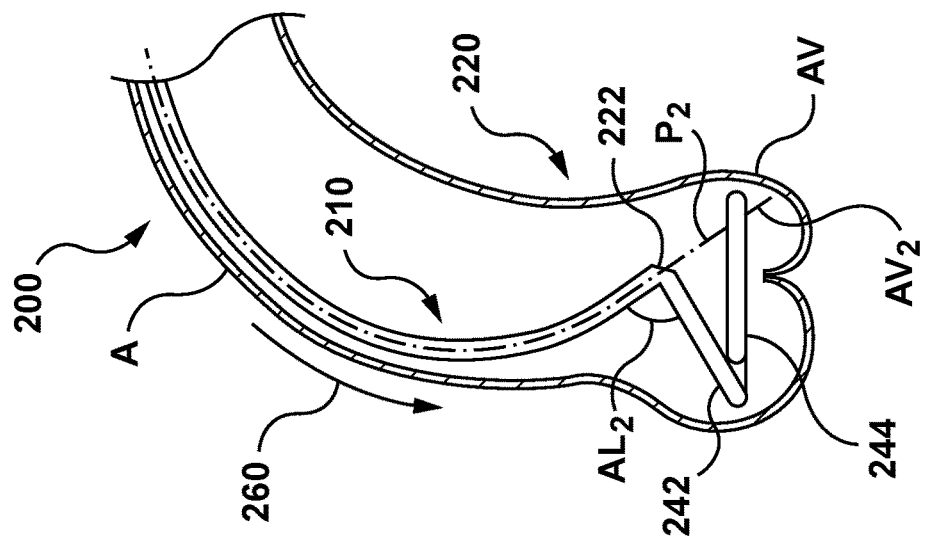
Figure 5A:
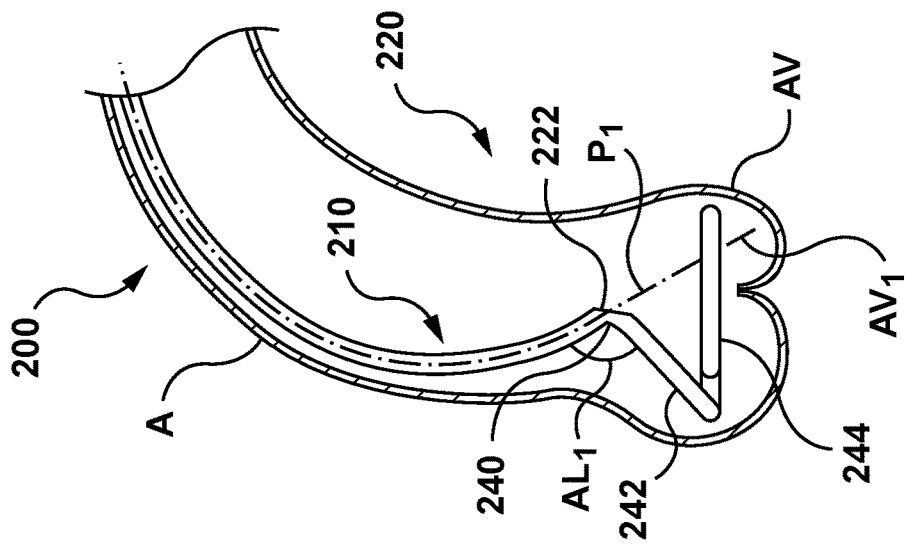

FIGS. 5A-5C are partial side views of the catheter 200 showing the alignment assembly 220 deployed within the aorta A of a patient and illustrating steps in a method for adjusting a guidewire path P (shown as dotted lines $P_1$, $P_2$ and $P_3$, respectively) through the central space 248 of the circumferential segment 244 (which substantially forms a loop shape) and across the aortic valve AV. Referring to FIG. 5A, an angle $A_{L1}$ is formed between a portion of the tubular component 210 proximally adjacent to the side port 222 and the longitudinal segment 242 of the alignment assembly 220, which distally extends from the side port 222. In an embodiment, the angle $A_{L1}$ may be formed by the bend 240, which may be considered to extend between the portion of the tubular component 210 proximally adjacent to the side port 222 and the longitudinal segment 242 distally adjacent to the side port 222. When the alignment assembly 220 is positioned with respect to the native anatomy as shown in FIG. 5A, the bend 240 forms the angle $A_{L1}$ and the guidewire path $P_1$ is projected to cross the aortic valve AV at point $AV_1$. To adjust the alignment assembly 220 to alter the guidewire path P, a clinician can push or pull the proximal segment (not shown) of the catheter 200 to adjust the angle $A_L$ and thereby the guidewire path P. For example, a clinician can push the proximal segment (not shown) of the catheter 200 in a distal direction (e.g., along arrow 260) to decrease the angle degree to angle $A_{L2}$ (FIG. 5B). The angle $A_{L2}$ alters the trajectory of the guidewire path P from the side port 222 to the guidewire path $P_2$. As illustrated, a guidewire (not shown) following the guidewire path $P_2$ would cross the aortic valve AV at point $AV_2$. Likewise, a clinician can pull the proximal segment (not shown) of the catheter 200 in a proximal direction (e.g., in the direction of arrow 262) to increase the angle degree to angle $A_{L3}$ (FIG. 5C). The angle $A_{L3}$ alters the trajectory of the guidewire path P along guidewire path $P_3$ which crosses the aortic valve AV at point $AV_3$. With reference to FIGS. 5A-5C together, a clinician can, in real time, determine a desired target point at which to cross the aortic valve AV (e.g., at a center of the valve, at a region of leaflet coaptation, etc.) and push or pull the proximal segment of the catheter 200 to adjust the angle $A_L$ and thereby adjust the guidewire path P of a subsequently advanced guidewire exiting the side port 222.

Referring back to FIG. 4D, the alignment assembly 220 is shown positioned within the aorta A downstream of the aortic valve AV, and the tubular component 210 of the catheter 200 is shown in an intravascular path extending from the aortic arch AA. Intravascular access to the aortic arch AA and ascending aorta A can be achieved via a percutaneous access site in a femoral, brachial, radial, or axillary artery to the targeted treatment site adjacent the aortic valve AV. Referring to FIGS. 3 and 4D together, and as is known in the art, a section of the proximal portion 112 (FIG. 3) of the tubular component 110, 210 is exposed externally of the patient even as the alignment assembly 120, 220 has been advanced fully to the targeted site in the patient. By manipulating the proximal portion 112 (FIG. 3) of the tubular component 110, 210 from outside the intravascular path, the clinician may advance the tubular component 110, 210 through the sometimes tortuous intravascular path and remotely manipulate the distal portion 114, 214 of the shaft 110, 210.

With reference to FIGS. 3, 4A and 4D together, the alignment assembly 120, 220 can extend intravascularly to the target site over the guidewire 102, 202 using an OTW technique (FIG. 3). As noted previously, the distal end 113, 213 of the tubular component 110, 210 and/or alignment assembly 120, 220 may define a lumen 128, 228 or passageway for receiving the guidewire 102, 202 (e.g., via the distal opening 118, 218) for delivery of the catheter 100, 200 using either OTW or RX techniques. At the treatment site, the guidewire 102, 202 can be at least partially axially withdrawn or removed, and the alignment assembly 120, 220 can transform or otherwise be moved to a deployed arrangement having the loop configuration as described above with respect to FIGS. 3-4D. The guidewire 102, 202 may comprise any suitable medical guidewire sized to slidably fit within the lumen 128, 228 of tubular component 110, 210 and/or other features of the catheter 100, 200, such as the handle 104 (FIG. 3). In one particular embodiment, for example, the guidewire 102, 202 may have a diameter of 0.356 mm (0.014 inch). In other embodiments, the alignment assembly 120, 220 may be delivered to the target site within a guide or straightening sheath (not shown) with or without using the guidewire 102, 202. When the alignment assembly 120, 220 is at the target site, the straightening sheath may be at least partially withdrawn or retracted and the alignment assembly 120, 220 can be transformed into the deployed arrangement. In still other embodiments, the tubular component 110, 210 may be steerable itself such that the alignment assembly 120, 220 may be delivered to the target site without the aid of the guidewire 102, 202 and/or straightening sheath.

With continued reference to FIGS. 3 and 4D together, image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the alignment assembly 120, 220 at the target site. In some embodiments, image guidance components (e.g., IVUS, OCT) can be integrated with the catheter 100, 200, the tubular component 110, 210 and/or run in parallel with the catheter 100, 200 to provide image guidance during positioning and deployment of the alignment assembly 120, 220, crossing of the heart valve with the guidewire 102, 202 and/or removal of the alignment assembly 120, 220. In a particular example, image guidance components (e.g., IVUS or OCT) can be coupled to at least the alignment assembly 120, 220 to provide three-dimensional images of the vasculature proximate the target site to facilitate positioning or deploying the alignment assembly 120, 220 within the target site (e.g., with the aorta proximate to the aortic valve).

Figure 6A:
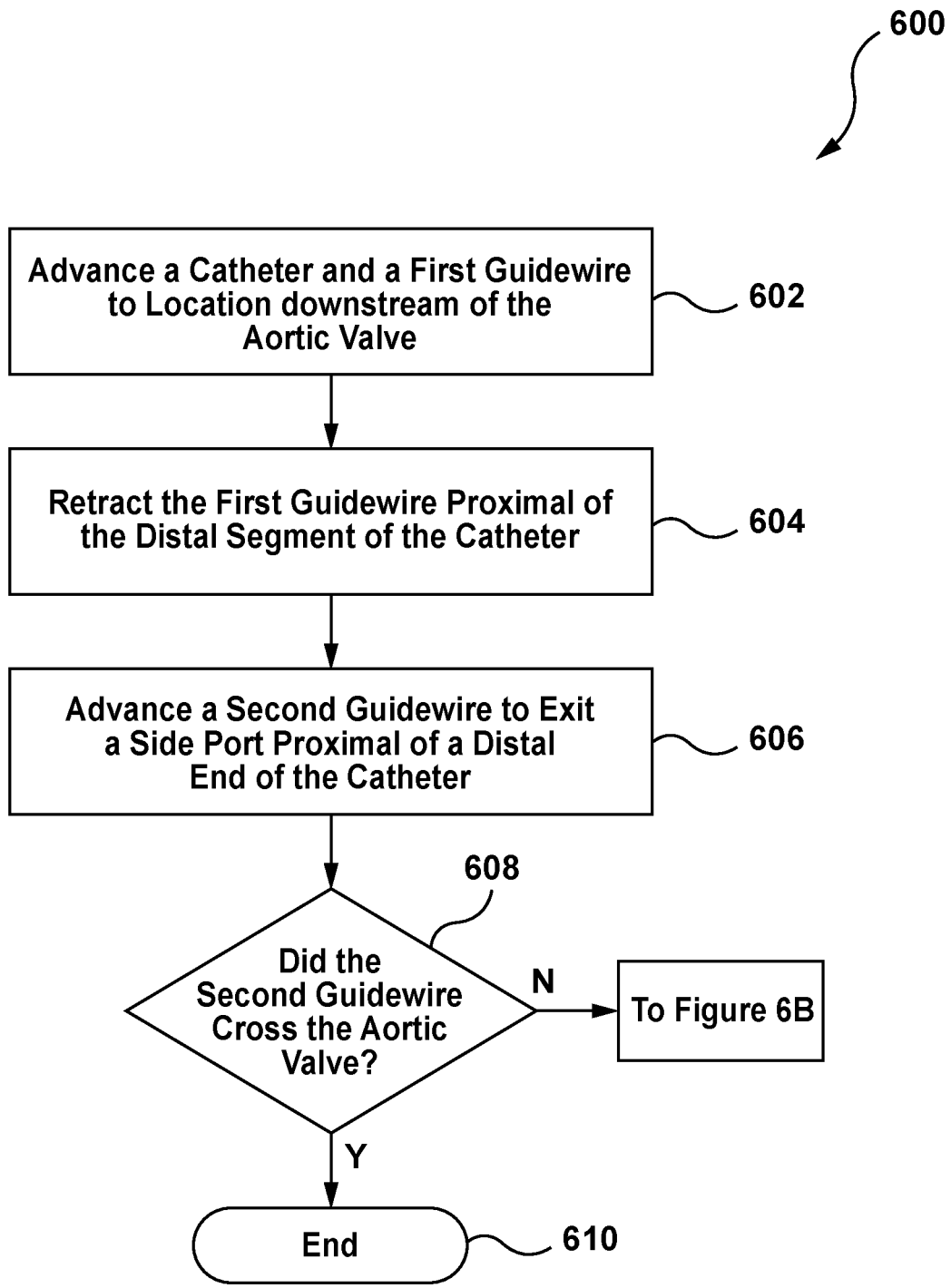
FIG. 6A is a flow diagram illustrating a method for crossing an aortic valve with a guidewire in a patient using the catheter of FIG. 4A and in accordance with an embodiment hereof.

FIG. 6A is block diagram illustrating a method 600 of crossing an aortic valve with a guidewire in a patient with the catheter 200 described above with reference to FIGS. 4A-5C and in accordance with an embodiment of the present technology. Referring to FIG. 6A (and with additional reference to FIGS. 4A-5C), the method 600 can include advancing a catheter 200 and a first guidewire 202a (illustrated 202 in FIG. 4A) through the vasculature of a patient to a location downstream of the aortic valve (block 602). In one embodiment, the first guidewire 202a is disposed in a proximal segment (not shown) and a distal segment 214 of the catheter 200 such that the catheter 200 conforms to the shape of the first guidewire 202a. In a particular example, the first guidewire 202a conforms or holds the proximal and distal segments 214 in a low profile delivery configuration.

The method 600 can also include retracting the first guidewire 202a proximal of the distal segment (e.g., proximal of the side port 222) of the catheter 200 (block 604). Retraction of the first guidewire 202a in the proximal direction causes at least a portion of the distal segment of the catheter 200 (e.g., the alignment assembly 220) to deploy or transform to a loop configuration, such as to bring the distal segment 214 of the tubular component 210 in apposition with a wall or walls of a vessel (e.g., aorta) adjacent to the aortic valve. The method 600 can further include distally advancing a second guidewire 202b such that the second guidewire 202b exits the side port 222 proximal of a distal end 213 of the alignment assembly 220 towards the leaflets of the aortic valve (block 606). In one embodiment, the advancing step is performed during systole of the cardiac cycle (e.g., when the leaflets of the aortic valve are substantially open). In some embodiments, the second guidewire 202b can be the same as the first guidewire 202a. For example, the first guidewire 202a can be retracted in a proximal direction (e.g., proximal of the distal segment 214) but not removed from the tubular component 210. Following deployment of the alignment assembly 220, the first guidewire 202a can be advanced distally to exit the port 222. In other embodiments, the first guidewire 202a can be a J-tip guidewire for positioning the catheter 200 at the target location proximal to the aortic valve and the second guidewire 202b is a straight-tip guidewire for crossing the aortic valve.

Following the step of advancing the second guidewire 202b (block 606), a clinician can assess if the second guidewire successfully crosses the aortic valve (decision block 608). If the clinician determines that the second guidewire 202b crosses the aortic valve, the method 600 can end (block 610). In some embodiments, the catheter 200 can be removed from the patient after crossing the aortic valve with the second guidewire 202b. If the second guidewire 202b did not advance between the leaflets of the aortic valve, the process can continue with a method 650 as illustrated in FIG. 6B (with additional reference to FIGS. 4A-5C).

Figure 6B:
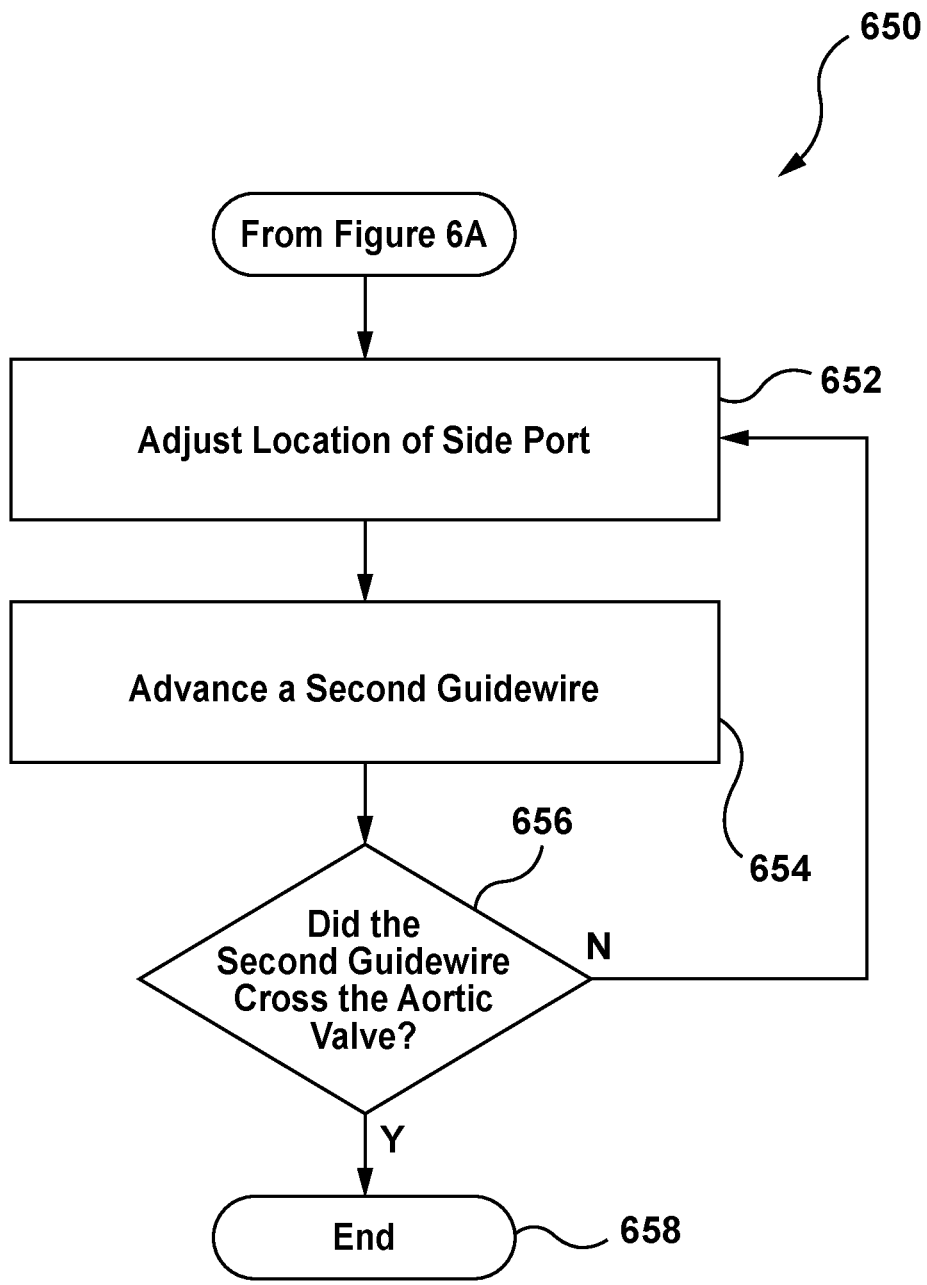
FIG. 6B is a flow diagram illustrating another method for crossing the aortic valve with a guidewire in a patient using the catheter of FIG. 4A and in accordance with an embodiment hereof.

Referring to FIG. 6B, the method 650 can include adjusting the location of the side port 222 relative to a center of the aortic valve (block 652). In one embodiment, a clinician can cause the side port 222 to be adjusted relative to the center (or to a region of leaflet coaptation) of the aortic valve by pulling or pushing on a proximal segment (not shown) of the catheter 200 in a proximal or distal direction, respectively (see FIGS. 5A-5C). By pulling or pushing on the proximal segment, the guidewire path from the side port 222 (and through the loop shape created by the alignment assembly 220) can be altered at least along a single axis across the aortic valve. After adjusting the location of the side port 222, the method 650 can include advancing the second guidewire 202b again (block 254). Following the step of advancing the second guidewire 202b (block 654), the clinician can again assess if the second guidewire 202b successfully crosses the aortic valve (decision block 656). If the clinician determines that the second guidewire 202b has crossed the aortic valve, the method 650 can end (block 658). If the second guidewire 202b did not advance between the leaflets of the aortic valve, the process can continue back to block 652 with adjusting the location of the side port 222 (as illustrated in FIG. 6B), and the method 650 concludes (block 658) when the second guidewire crosses the aortic valve. Following advancement of the second guidewire 202b between the leaflets of the aortic valve, the catheter 200 can be retracted through the vasculature and removed from the patient.

Additional Embodiments of Catheters Having Shape Set Loop Configurations

Figure 7A:
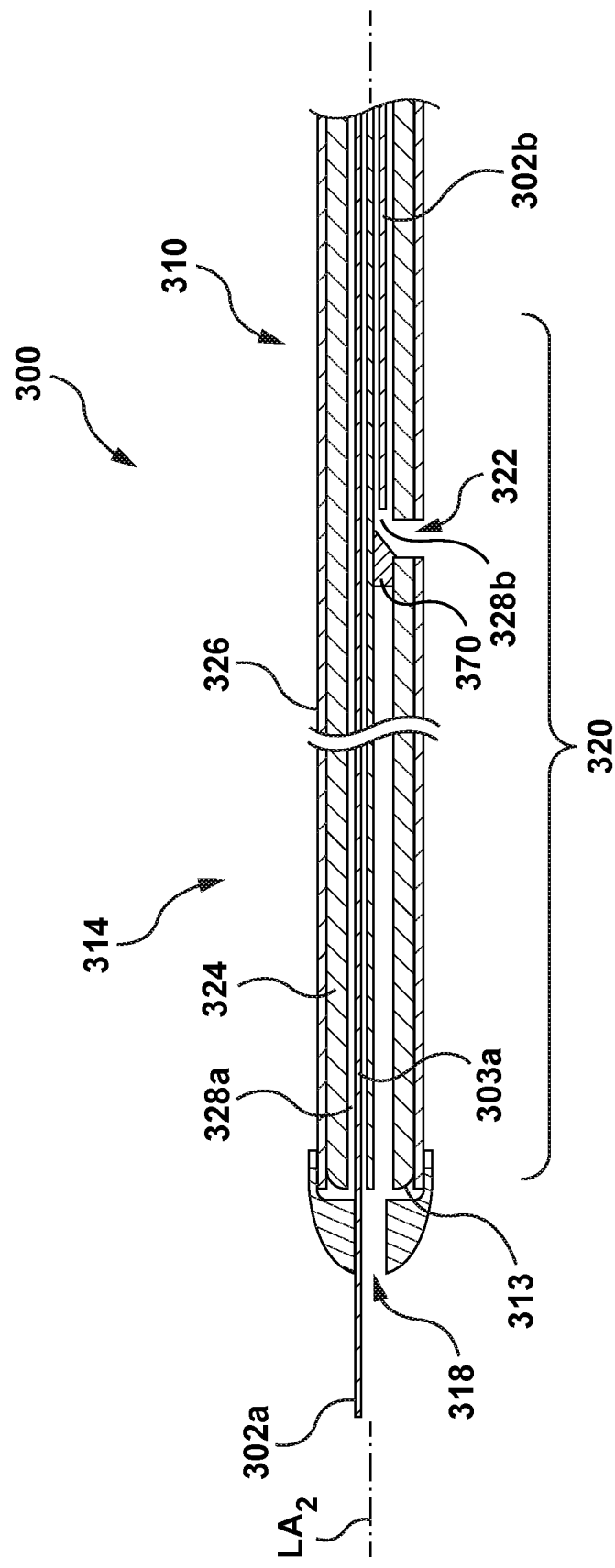
FIG. 7A is an enlarged sectional view of a distal segment of a catheter with an intravascular alignment assembly in a delivery state (e.g., low-profile or collapsed configuration) in accordance with another embodiment hereof.
Figure 7B:
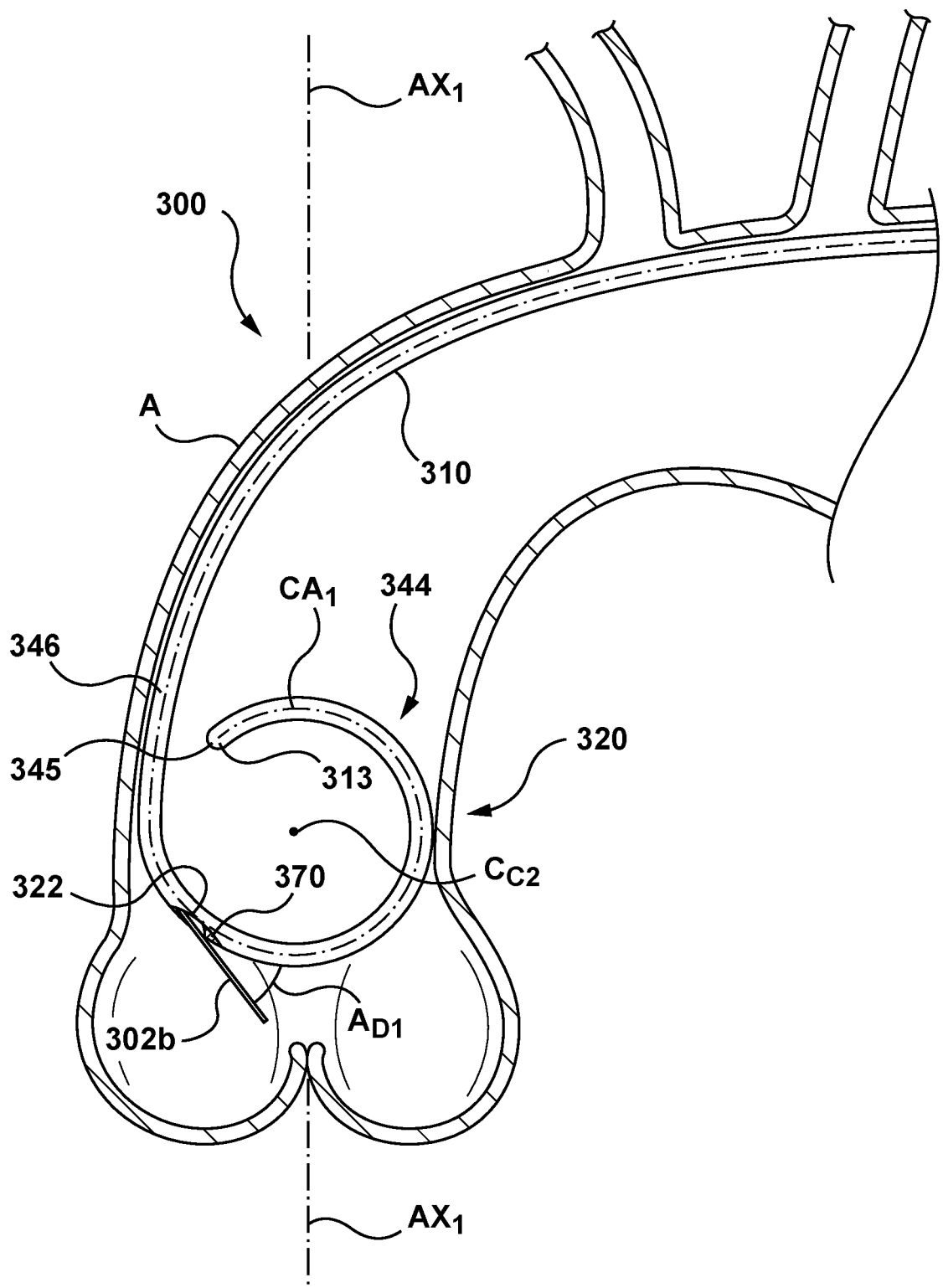
FIG. 7B illustrates a cut-away view of an aorta and aortic valve of a patient and showing a partial side view of the distal segment of the catheter of 7A and showing the alignment assembly in a deployed state (e.g., an expanded configuration) in accordance with an embodiment hereof.

FIG. 7A is an enlarged, longitudinal cross-sectional view of a distal segment 314 of an elongated hollow shaft or tubular component 310 of a catheter 300 having an alignment assembly 320 in a delivery state (e.g., a low-profile or collapsed configuration) and in accordance with another embodiment hereof. FIG. 7B illustrates a cut-away view of an aorta A and an aortic valve AV of a patient and a partial side view of the distal segment 314 of the catheter 300 of FIG. 7A with the alignment assembly 320 in a deployed state (e.g., an expanded configuration). The catheter 300 includes features generally similar to the features of the catheter 200 described above with reference to FIGS. 4A-5C. For example, the catheter 300 includes the tubular component 310 and the alignment assembly 320 at the distal segment 314 of the tubular component 310. Additionally, the alignment assembly 320, as discussed above with respect to the alignment assembly 220, can be transformed or actuated between the delivery state (FIG. 7A) and the deployed state having a shape set or pre-formed loop (or other coiled, helical/spiral) configuration (FIG. 7B). However, the alignment assembly 320 differs from the alignment assembly 220 in that a shape set loop configuration achieved by the alignment assembly 320 directs the distal segment 314 of the tubular component 310 to loop or coil in a proximal direction, or stated another way, loop back towards the proximal segment (not shown) of the tubular component 310. Accordingly, the loop feature of the alignment assembly 320 is configured to be deployed in a vertical orientation along the ascending aorta (e.g., parallel to a longitudinal axis $LA_2$ of the catheter 300; FIG. 7A).

Referring to FIG. 7A, the alignment assembly 320 includes an alignment member 324 disposed within a covering 326. In another arrangement, the alignment member 324 can have a coating over a surface of the alignment member 324. In other arrangements, the catheter 300 and/or the alignment assembly 320 may not include the covering 326. The tubular component 310 can include a first lumen 328a for accommodating a first guidewire 302a and a second lumen 328b for accommodating a second guidewire 302b. In one embodiment, the first guidewire 302a can be a positioning guidewire (e.g., a J-tip guidewire or other medical guidewire) used to direct the catheter 300 through the vascular and to the target location within the aorta and adjacent to (e.g., downstream of) the aortic valve. The first lumen 328a, provided for slidably receiving the first guidewire 302a during delivery or removal of the alignment assembly 320 (FIG. 7A), can span between a first opening (not shown) at a proximal end of the catheter 300 and a second opening 318 at the distal end 313 of the tubular component 310. As such, the alignment assembly 320 may be restrained in the delivery state (FIG. 7A) with the first guidewire 302a disposed within the lumen 328a. In other embodiments, a straightening sheath, guide catheter, or other straightening device may be used in lieu of the first guidewire 302a to retain the alignment assembly 320 in the delivery state.

Referring to FIGS. 7A and 7B together, when the first guidewire 302a is retracted proximal of the alignment assembly 320, the alignment member 324 provides a shape-recovery force sufficient to overcome the straightening force provided by a distalmost portion 303a of the first guidewire 302a such that the alignment assembly 320 can deploy into its shape set curved or looped (or, alternatively, coil, helical/spiral-shaped) configuration. As illustrated in FIG. 7B, the loop configuration of the alignment member 324 is defined by a circumferential segment 344 initiating at an origin or proximal end 346 and extending through a terminal end 345, which is also the distal end 313 of the tubular component 310, and which curves about a center of curvature $C_{C2}$. In the embodiment illustrated in FIG. 7B, an axis line (not shown) drawn through the center of curvature $C_{C2}$ is substantially perpendicular to the longitudinal axis $LA_2$ (FIG. 7A) and to a central axis $A_{X1}$ of the ascending aorta A. Also in this embodiment, by way of example and not limitation, the terminal end 345 of the circumferential segment 344 does not align with the origin 346 and is disposed relative thereto in a direction radially inward toward the center of curvature $C_{C2}$. Further winding of the circumferential segment 344 (e.g., by pushing the proximal segment (not shown) of the catheter 300 in the distal direction) would result in additional coils or loops having increasingly smaller pitch being formed. In some embodiments, the loop configuration can have concentric winding wherein additional numbers of loops or coils having the progressively smaller pitch can be formed. At least a portion of the circumferential segment 344 defining the outside loop of the coil (if additional coils are present) can engage an inner wall of the aorta A for stabilizing and/or orienting the alignment assembly within the aorta.

In some embodiments, the distalmost portion 303a of the first guidewire 302a can remain at least partially within the alignment assembly 320 (e.g., proximal to the origin 346 of the circumferential segment 344) while in the deployed state (e.g., FIG. 7B), such that the first guidewire 302a can impart additional structural integrity to the positioning of the alignment assembly 320 when it is in a loop configuration prior to a subsequent advancement of the second guidewire 302b within the second lumen 328b and through a side port 322 in a direction generally toward the aortic valve leaflets. As discussed with respect to the catheter 200, this feature may provide additional stability and proper alignment to the alignment assembly 320 during the cardiac cycle and/or during placement of the second guidewire 302b across the aortic valve. After successfully crossing the aortic valve AV with the second guidewire 302b, the first guidewire 302a may be re-advanced through the first lumen 328a to at least partially straighten the alignment assembly 320 (e.g., transition the alignment assembly 320 from the deployed state to the delivery state) prior to removal of the catheter 300 from the vasculature. In other embodiments, at least partial advancement of the first guidewire 302a through the first lumen 328a can be used to reposition or reorient the alignment assembly 320 during attempts to cross the aortic valve with the second guidewire 302b. In still other embodiments, the first guidewire 302a can be removed from the alignment assembly 320 and/or the tubular component 310 entirely.

The alignment assembly 320 also includes the side port 322 being formed through each of the coating 326 and the alignment member 324 to provide a guidewire exit path from the second lumen 328b to an exterior of the alignment assembly 320 when the alignment member 324 is deployed (FIG. 7B). In operation, and when in the delivery state, the second guidewire 302b is not advanced beyond the side port 322 (FIG. 7A). Once the alignment assembly 320 is deployed, the side port 322 is positioned along an outside curve of the circumferential segment 344 and generally oriented toward the aortic valve (FIG. 7B). Advancement of the second guidewire 302b in the distal direction causes the second guidewire 302b to exit the side port 322 and continue in the direction of the aortic valve AV. In the arrangement shown in FIGS. 7A and 7B, the second lumen 328b terminates at the side port 322 and the alignment assembly 320 further includes a deflector 370 at the termination of the second lumen 328b to deflect the second guidewire 302b towards the side port 322. In one embodiment, the deflector 370 can be a slanted surface (e.g., a 45° slant or other slant) facing at least partially toward the side port 322 and which causes the second guidewire 302b to deflect (e.g., change course) from its travel along the guidewire path provided by the second lumen 328b and to thereby exit from the side port 322 in a non-axial direction. The deflector 370 may change the course of the direction of the second guidewire 302b by a defined deflection angle $A_{D1}$. In a particular example, the deflection angle $A_{D1}$ can be about 45°. In other embodiments, the deflection angle $A_{D1}$ can be between about 15° and about 90°. In some arrangements, the deflector 370 can be a separate component of the alignment assembly 320 that is coupled to and/or retained within a terminal portion of the second lumen 328b. For example, the deflector can be a metal, plastic, rubber, or other molded material for providing the slanted deflective surface at the side port 322. In other embodiments, the deflector 370 may be integral with the alignment member 324.

In other embodiments, the second lumen 328b may not include a deflector 370. In these embodiments, the curve of the circumferential segment 344, at least at the location of the side port 322, may be sufficient to allow the second guidewire 302b to advance through a portion of the second lumen 328b proximal to the side port 322 and to then exit via the side port 322. In an embodiment, a curved portion of the lumen 328b may be continuous with the side port 322 such that distal advancement of the second guidewire 302b through the second lumen 328b would eventually cause the tip of the second guidewire 328b to exit through the side port 322 and continue toward the central region of the aortic valve, when the alignment assembly 320 is in the deployed state. For example, the side port 322 is in an open configuration when the alignment assembly 320 is in the deployed state such that the guidewire path is aligned with the side port 322 and exits the alignment assembly 320 in a non-axial or non-collinear direction to a curvilinear axis $CA_1$ defined by the circumferential segment 344 when the alignment member 324 is in a loop configuration (FIG. 7B).

In some embodiments, the tubular component 310 and alignment assembly 320 may only include a single lumen 328 and the first guidewire 302a may or may not be the same as the second guidewire 302b. For example, the same guidewire 302a that is used to deliver the alignment assembly 320 to the target location may also be able to exit the side port 322 (e.g., the guidewire 302a can be subsequently advanced following deployment of the alignment assembly 320). In other embodiments, the tubular component 310 and the alignment assembly 320 may only include a single lumen 328 but the features of the first and second guidewires 302a, 302b may be different. For example, a first guidewire 302a used for delivery may be a J-tip guidewire and the second guidewire 302b used to cross the aortic valve may be a straight-tip guidewire. In further examples, the second guidewire 302b may be more flexible than the first guidewire 302a.

Once the alignment assembly 320 is deployed, a clinician may be able to visually detect (e.g., using image guidance as discussed above) if the orientation of the guidewire path from the side port 322 is aligned with the center region (e.g., a leaflet coaptation region) of the aortic valve. If during advancement of the second guidewire 302b or before, it is determined that the guidewire path needs adjustment, the clinician can adjust the location of the side port 322 relative to the aortic valve by pushing or pulling on the proximal segment (not shown) of the tubular component 310.

Figure 8:
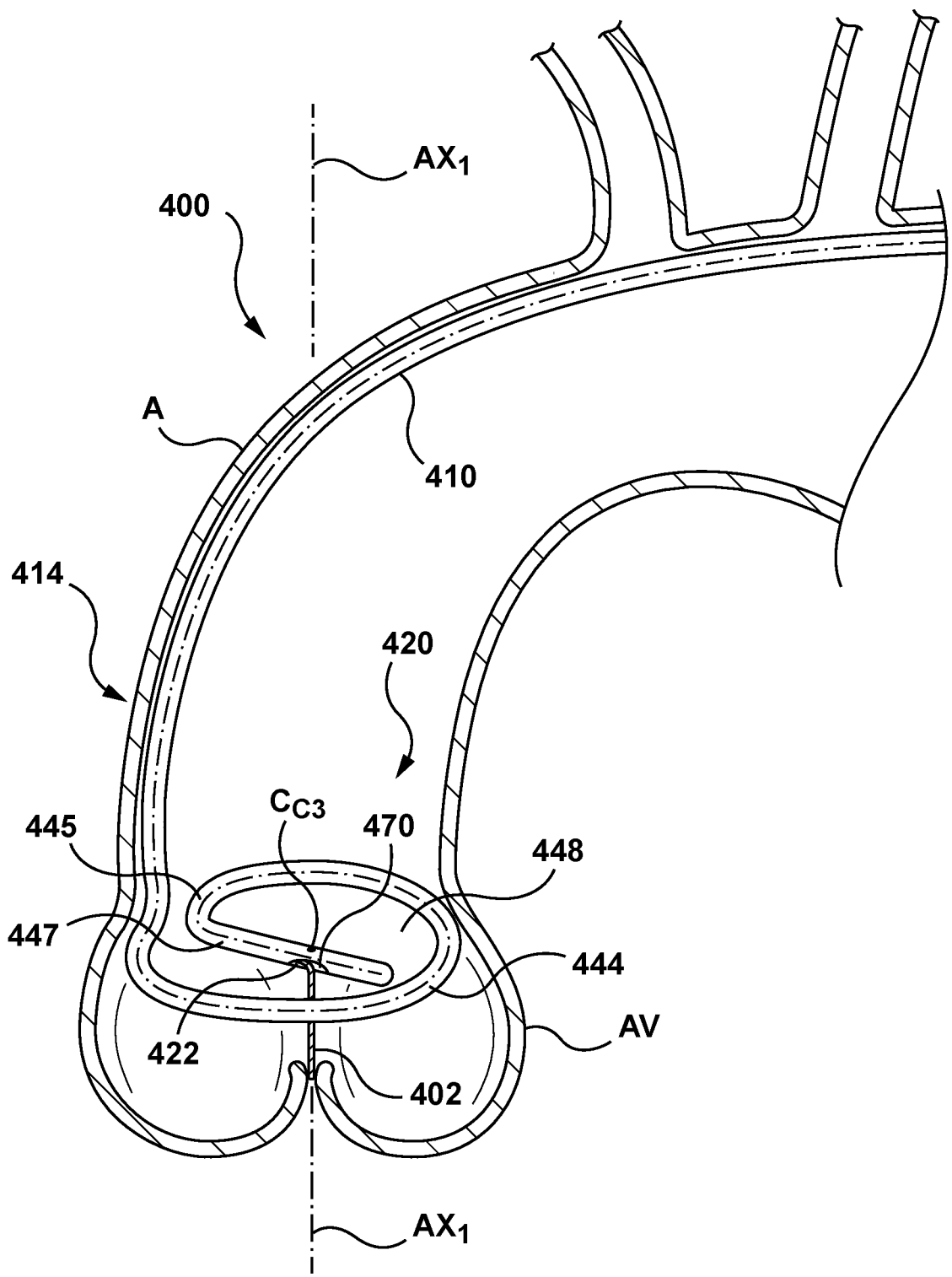
FIG. 8 is a perspective view of a distal segment of a catheter with an intravascular alignment assembly in a deployed state (e.g., an expanded configuration) adjacent an aortic valve in a patient in accordance with a further embodiment hereof.

FIG. 8 is a perspective view of a distal segment 414 of an elongate shaft 410 of a catheter 400 with an intravascular alignment assembly 420 in a deployed state (e.g., an expanded configuration) adjacent an aortic valve AV in a patient in accordance with a further embodiment hereof. The catheter 400 includes features generally similar to the features of the catheters 200, 300 described above with reference to FIGS. 4A-7B. For example, the catheter 400 includes the tubular component 410 and the alignment assembly 420 at the distal segment 414 of the tubular component 410. Additionally, the alignment assembly 420, as discussed above with respect to the alignment assembly 220, can be transformed or actuated between the delivery state (not shown) and the deployed state having a shape set loop (or other coiled, helical/spiral) configuration (FIG. 8). For example, the catheter 400 can be delivered to the target region within the aorta A and downstream of the aortic valve AV while maintained in the delivery state using OTW approach as described. In another embodiment, a straightening sheath can be used to maintain the low-profile configuration during delivery.

As illustrated, the loop configuration of the alignment assembly 420 has similarities to the loop configuration of the alignment assembly 220 shown in FIGS. 4B-4D. For example, an axis line (not shown) drawn through a center of curvature $C_{C3}$ about which a circumferential segment 444 curves is substantially coincident with a central axis $A_{X1}$ of the ascending aorta A. However, the alignment assembly 420 differs from the alignment assembly 220 in that the loop configuration controlled by the shape set form of an alignment member (not shown) includes a distal tip segment 447 extending from a terminal end 445 of the circumferential segment 444 and which extends across a central space 448 created by the circumferential segment 444.

As shown in FIG. 8, the alignment assembly 420 also includes a side port 422 disposed within the distal tip segment 447 that is oriented to guide a guidewire 402 towards the leaflet coaptation region of the aortic valve AV. The guidewire 402 is sufficiently flexible such that it will tend to conform to the loop configuration of the alignment member (not shown). The guidewire 402 is slidably received within a guidewire lumen (not shown) defined by the tubular component 410 and the alignment member 420 and which terminates at the side port 422. The side port 422 can include a deflector 470, which can be similar to the deflector 370 of the catheter 300. The deflector 470 can control the exit trajectory of the guidewire 402 from the lumen and through the aortic valve AV as shown in the FIG. 8. The tubular component 410 and the alignment assembly 420 may have more than one lumen (e.g., as illustrated in the embodiment of the catheter 300 shown in FIG. 7A), such as, for example, for slidably receiving a delivery guidewire (not shown) in an OTW approach, and for accommodating the guidewire 402 across the aortic valve.

Selected Embodiments of Catheter Assemblies Having a Plurality of Side Ports

Figure 9A:
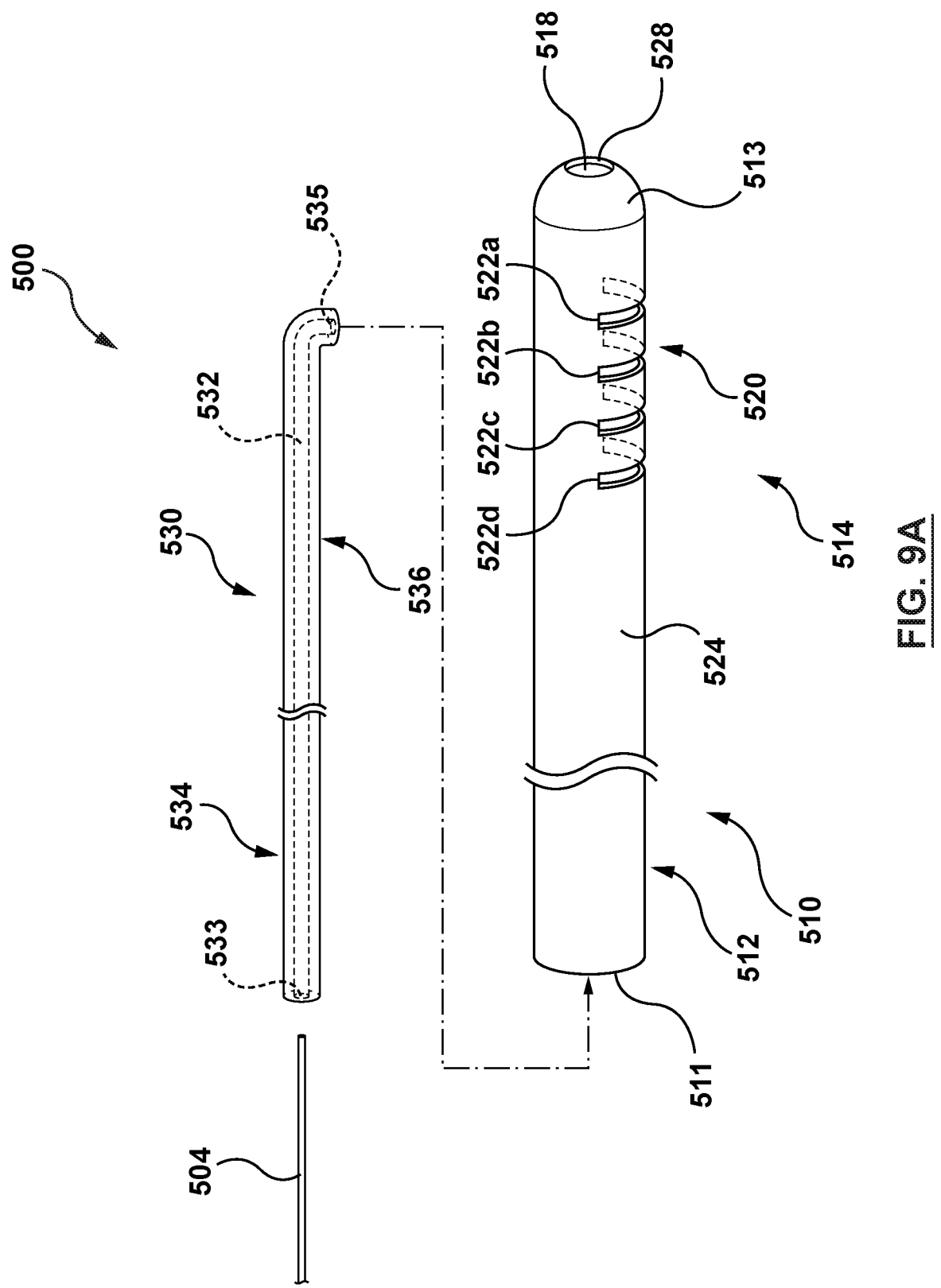
FIG. 9A is an exploded view of a distal segment of a catheter assembly in accordance with another embodiment hereof.

FIG. 9A is an exploded view of a catheter assembly 500 ("catheter 500") having an elongated hollow shaft or tubular component 510 and an alignment assembly 520 for delivering a guidewire 504 across a heart valve in accordance with another embodiment hereof, and FIG. 9B is an enlarged sectional view of the alignment assembly 520 of the catheter 500 shown in FIG. 9A. As noted for some of the embodiments of the alignment assemblies 120 discussed above with reference to FIG. 3, the alignment assembly 520 can include a tubular outer support structure 524 having a plurality of side ports 522a-522d spaced-apart along a distal segment 514 of the tubular component 510.

Referring to FIGS. 9A and 9B together, the catheter 500 has the tubular, tubular component 510 having a proximal end 511 at an origin of a proximal segment 512 and a distal end 513 at a terminus of the distal segment 514. The alignment assembly 520 is located along the distal segment 514 and is configured to be located at the target location within the aorta downstream of the aortic valve. The tubular component 510 can be a generally hollow body having a lumen 528 for accommodating a delivery or first guidewire 502 (e.g., shown as a J-tip guidewire in FIG. 9B) through a distal opening 518 and a proximal opening (not shown) using an OTW arrangement. In another embodiment, the tubular component 510 of the catheter 500 may be configured to be steerable such that the alignment assembly 520 may be delivered to the target site without the aid of the first guidewire 502.

The alignment assembly 520 includes an outer body, such as the support structure 524 that can be integral with tubular component 510, as shown in FIG. 9B, or in another arrangement, can be a component coupled to the tubular component 510 in a manner that permits the lumen 528 to be continuous between the tubular component 510 and the support structure 524. The support structure 524 can define a tubular structure having a low-profile outer dimension $D_3$ (e.g., circular or non-circular dimension), a longitudinal axis $LA_3$, and the lumen 528 for slidably receiving a guidewire, such as the first guidewire 502 (FIG. 9B), during delivery or removal of the alignment assembly 520. As described further below, the lumen 528 is disposed through the support structure 524 and the plurality of spaced apart side ports 522a-522d span the wall of the support structure 524 to provide various guidewire exit paths from the lumen 528 to an exterior of the alignment assembly 520 when the alignment assembly is located adjacent the aortic valve (discussed further below with respect to FIG. 10).

Referring back to FIGS. 9A and 9B, the alignment assembly 520 also includes a wire guide 530 that is slidably disposed within the support structure 524. The wire guide 530 can have a lumen 532 that is configured to slidably receive the second guidewire 504 (e.g., a guidewire for delivering across the aortic valve) through a proximal guidewire port 533 (shown as dotted line in FIG. 9A) disposed within a first portion 534 of the wire guide 530 and to direct the second guidewire 504 through a distal guidewire port 535 disposed at a terminal end of a second portion 536 of the wire guide 530. As shown best in FIG. 9B, the wire guide 530 is an elongate tubular structure configured or dimensioned to slide within the lumen 528 of the support structure 524, and to be slidable relative to the side ports 522a-522d. Axial movement of the wire guide 530 relative to the support structure 524 aligns the distal guidewire port 535 with one of the plurality of spaced-apart side ports 522a-522d. As shown in FIG. 9B, the distal guidewire port 535 is aligned with the side port 522b. Rotational movement of the wire guide 530 relative to the support structure 524 radially positions the distal guidewire port 535 allowing for alteration of a radial trajectory of a guidewire exiting from an axially aligned side port 522a-522d. In operation, a clinician can push or pull on the first portion 534 of the wire guide 530, or rotate from the first portion 534 of the wire guide 530, while holding the support structure 524 steady within the aorta. In alternative arrangements, the support structure 524 can be manipulated relative to the wire guide 530 by pushing or pulling on the proximal segment 512 of the tubular component 510 until the distal guidewire port 535 is aligned with the desired side port 522b. Once the distal guidewire port 535 is aligned with the desired side port 522 (e.g., side port 522b), the second guidewire 504 can be advanced through the lumen 532 to exit the aligned side port 522b.

As shown in FIGS. 9A and 9B, the plurality of spaced-apart side ports 522a-522d may be distributed on the support structure 524 in a desired arrangement. For example, the axial distances between the side ports 522a-522d may be provided to allow for selectivity in a preferred guidewire path when advancing a guidewire across the aortic valve in a variety of a patients having variable sized and shaped anatomy. Referring to FIG. 9B, the axial distance 523 may be in a range of between approximately 2 mm to approximately 1 cm. In a particular embodiment, the axial distance 523 may be in the range of approximately 2 mm to approximately 10 mm. In another embodiment, the side ports 522a-522d may be spaced apart approximately 30 mm from each other.

In the illustrated embodiment, the side ports 522a-522d are aligned circumferentially with each other along a length $L_3$ of the alignment assembly 520; however, in other arrangements, the side ports can be both longitudinally and circumferentially off-set from one another. FIG. 9A illustrates four side ports 522a-522d longitudinally spaced-apart from one another in a distal region of the alignment assembly 520; however, one of ordinary skill in the art will recognized that there can be more or less than four side ports 522 provided on support structure 524. In some embodiments, and as illustrated in FIG. 9A, the individual side ports 522a-522d can have the shape of a partial circumferential slot formed in the support structure 524, thereby allowing for alteration of a radial trajectory of a guidewire exiting from an aligned slot by rotation of the wire guide 530, and particularly the distal guidewire port 535, relative thereto. In other embodiments, not shown, the side ports 522a-522d can be circular, oblong, or other shaped holes disposed or formed in the support structure 524.

In one embodiment, the support structure 524 can include a solid structural element, e.g., a wire, tube, coiled or braided cable. The support structure 524 may be formed from biocompatible metals and/or polymers, including polyethylene terephthalate (PET), polyamide, polyimide, polyethylene block amide copolymer, polypropylene, or polyether ether ketone (PEEK) polymers. In some embodiments, components of the support structure 524 may be formed from stainless steel, nitinol, silver, platinum, nickel-cobalt-chromium-molybdenum alloy, or a combination of such materials. In one particular embodiment, for example, the support structure 524 can include a shape memory material, such as spring temper stainless steel or nitinol. Furthermore, in particular embodiments, the support structure 524 may be formed, at least in part, from radiopaque materials that are capable of being fluoroscopically imaged to allow a clinician to determine if the alignment assembly 520 is appropriately placed and/or deployed in the aorta and/or adjacent the aortic valve. Radiopaque materials may include, for example, barium sulfate, bismuth trioxide, bismuth subcarbonate, powdered tungsten, powdered tantalum, or various formulations of certain metals, including gold and platinum, and these materials may be directly incorporated into structural elements (e.g., at or aligned with side ports 522, the distal end 513 of the tubular component 510, etc.) or may form a partial or complete coating on the support structure 524.

Figure 10:
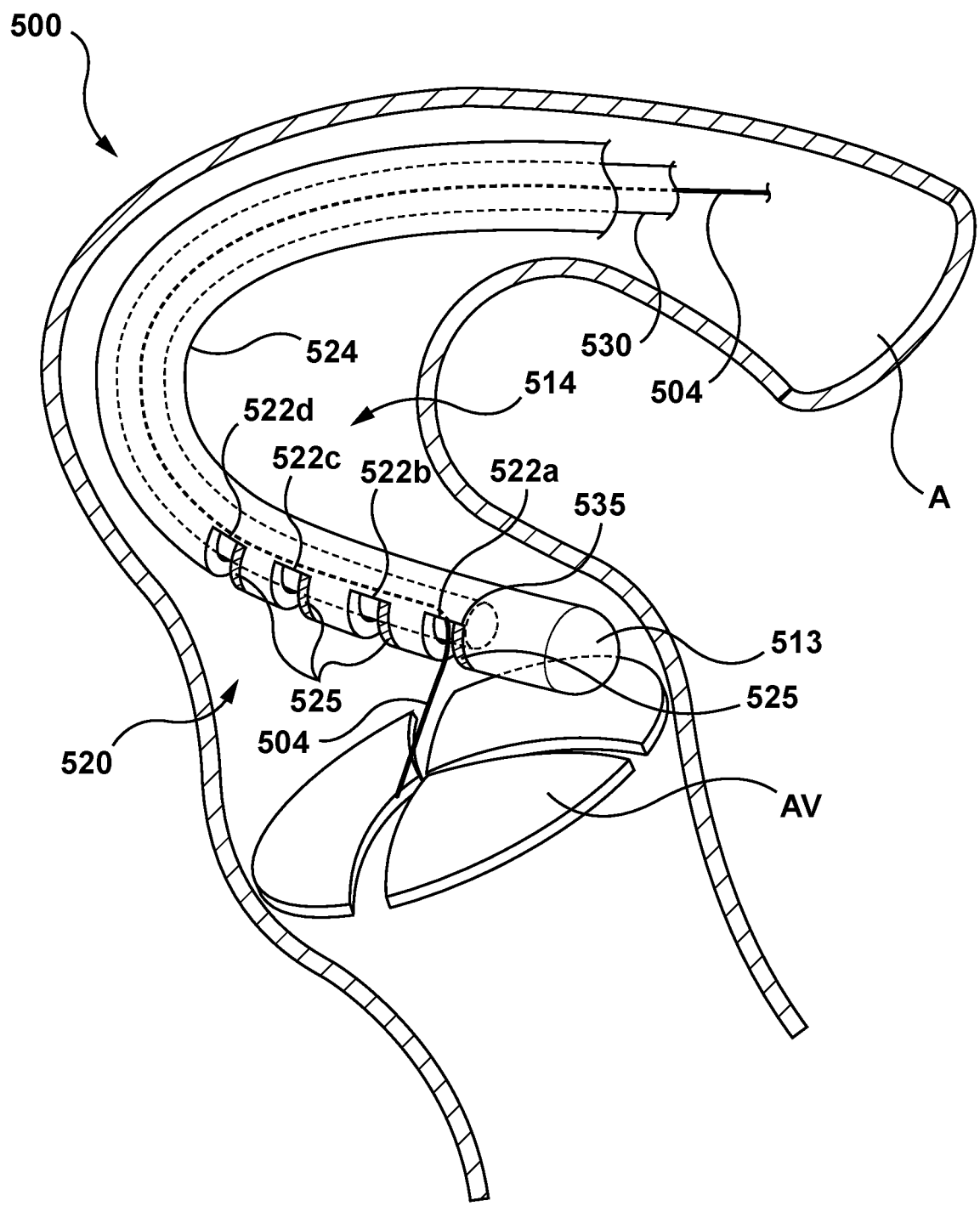
FIG. 10 is a perspective view of the distal segment of the catheter assembly of FIG. 9A within an aorta and adjacent to the aortic valve of a patient in accordance with a further embodiment hereof.

FIG. 10 is a perspective view of the distal segment 514 of the tubular component 510 of the catheter assembly 500 of FIG. 9A within an aorta A and adjacent to the aortic valve AV of a patient in accordance with a further embodiment hereof. As illustrated in FIG. 10, the alignment assembly 520 can be transluminally delivered using various arterial routes to the target location as described previously and as known in the art. The distal end 513 of the distal segment 514 can be placed against the native aortic valve annulus (e.g., along one edge of the annulus). Imaging guidance (e.g., fluoroscopy) can be used by the clinician to determine which side port 522a-522d is most likely to provide the desired guidewire path through the leaflet coaptation region of the aortic valve AV. In one embodiment, the side ports 522a-522d can have respective radiopaque markers 525 or sensors (not shown) for visualizing the location of and/or differentiating the side ports 522a-522d in situ. Once a side port 522a-522d is determined, the distal guidewire port 535 is axially aligned with the selected side port (e.g., side port 522a in FIG. 10), and the guidewire 504 can be advanced through the side port 522a and toward the aortic valve AV.

Figure 11:
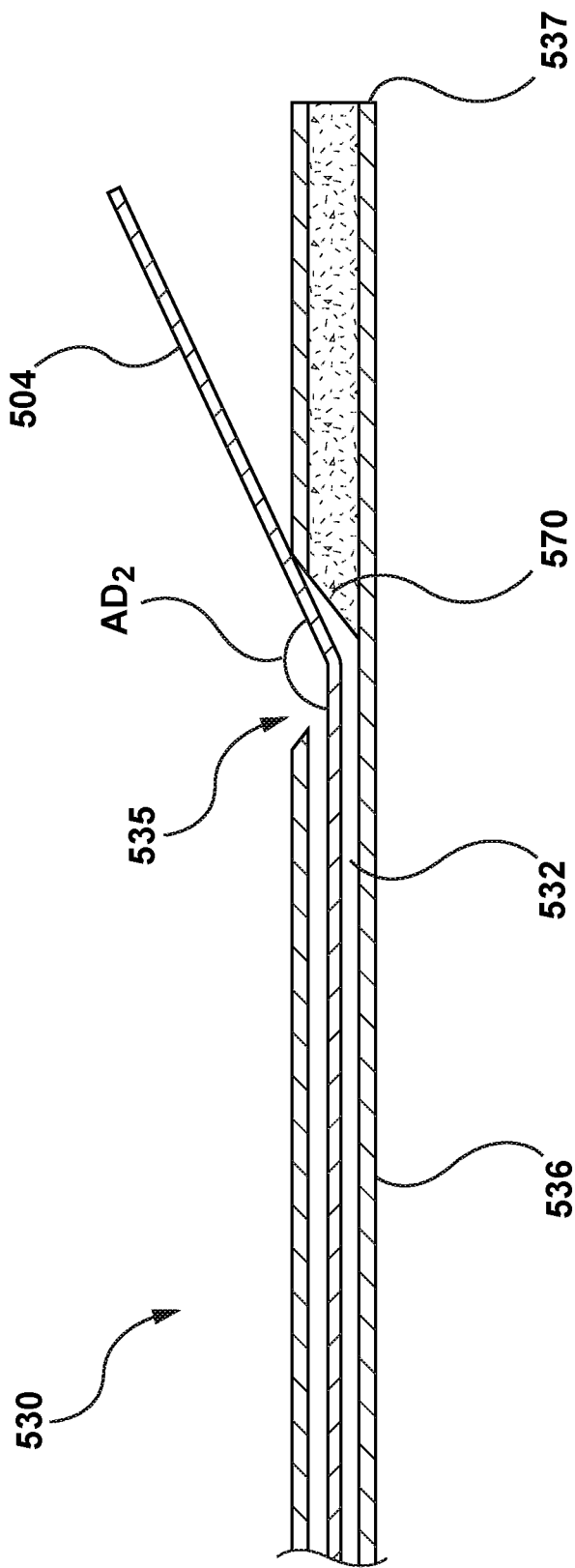
FIG. 11 is an enlarged sectional view of a distal portion of a wire guide with a deflector for directing a guidewire through a distal guidewire port at a deflection angle in accordance with an embodiment hereof.

Referring back to FIGS. 9A and 9B, the wire guide 530 can be provided with a pre-formed or shape set at the second portion to provide the distal guidewire port 535. For example, the wire guide 530 can have a bend or turn that orients the guidewire 504 to exit the lumen 532 and exit through the aligned side port 522. In other arrangements, however, the wire guide 530 is not pre-shaped or shape set to accommodate the desired redirection of the second guidewire 504 out of the lumen 532. FIG. 11 is an enlarged sectional view of the second portion 536 of a wire guide 530 with a deflector 570 for directing a guidewire 504 through the distal guidewire port 535 at a deflection angle $A_{D2}$ in accordance with an embodiment of the present technology. In the alternative embodiment illustrated in FIG. 11, the distal guidewire port 535 is disposed within the wire guide 530 in a location proximal of a distal end 537 of the second portion 536. The deflector 570 can be similar to the deflector 370 (FIG. 7A) discussed above with respect to the catheter 300. In one embodiment, the deflector 570 can reorient a guidewire 504 as it is distally advanced from the lumen 532 to exit a respective side port 522. In some instances, the deflector 570 can have a deflector surface angled at about 45° with respect to a longitudinal axis of the wire guide 530. In other embodiments, the deflector surface of the deflector 570 can have a different slant or angle that decreases or increases the deflection angle $A_D$.

Figure 12A:
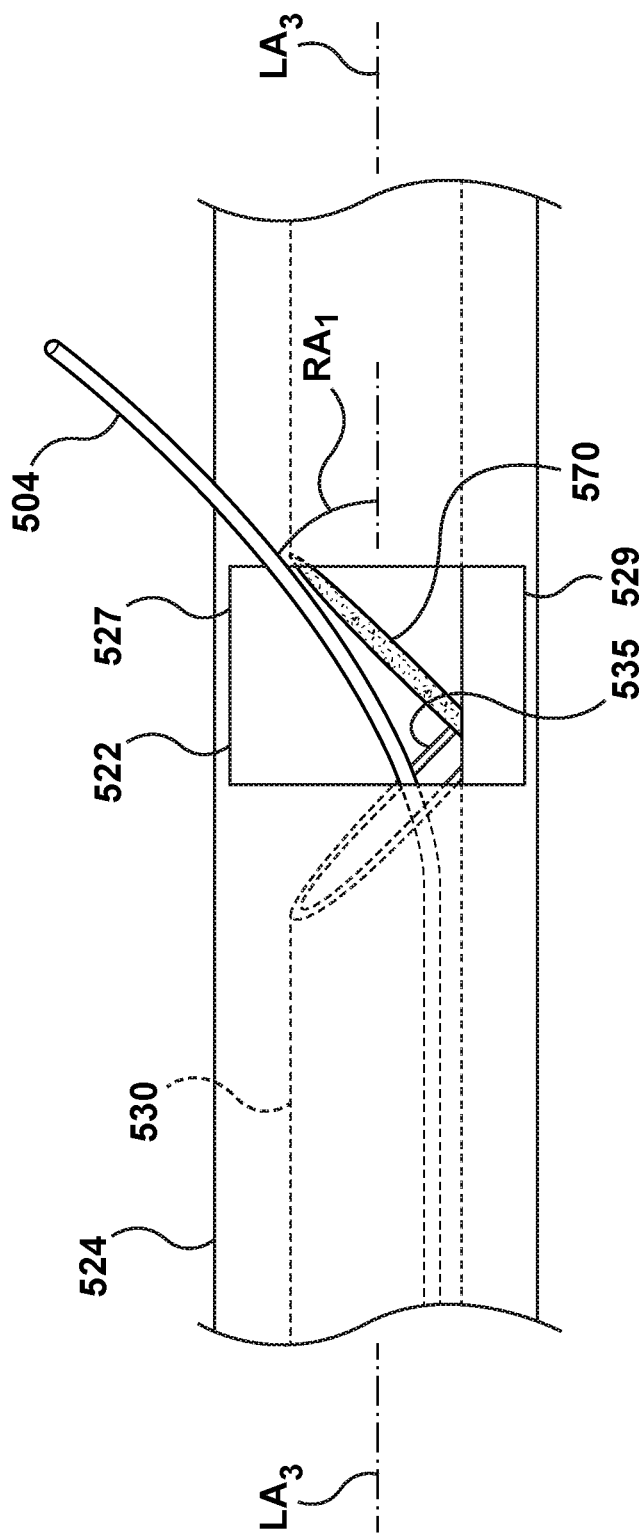
FIGS. 12A and 12B are an enlarged planar side views of the catheter assembly of FIG. 9A showing a guidewire exiting an aligned side port at various rotation angles in accordance with an embodiment hereof.
Figure 12B:
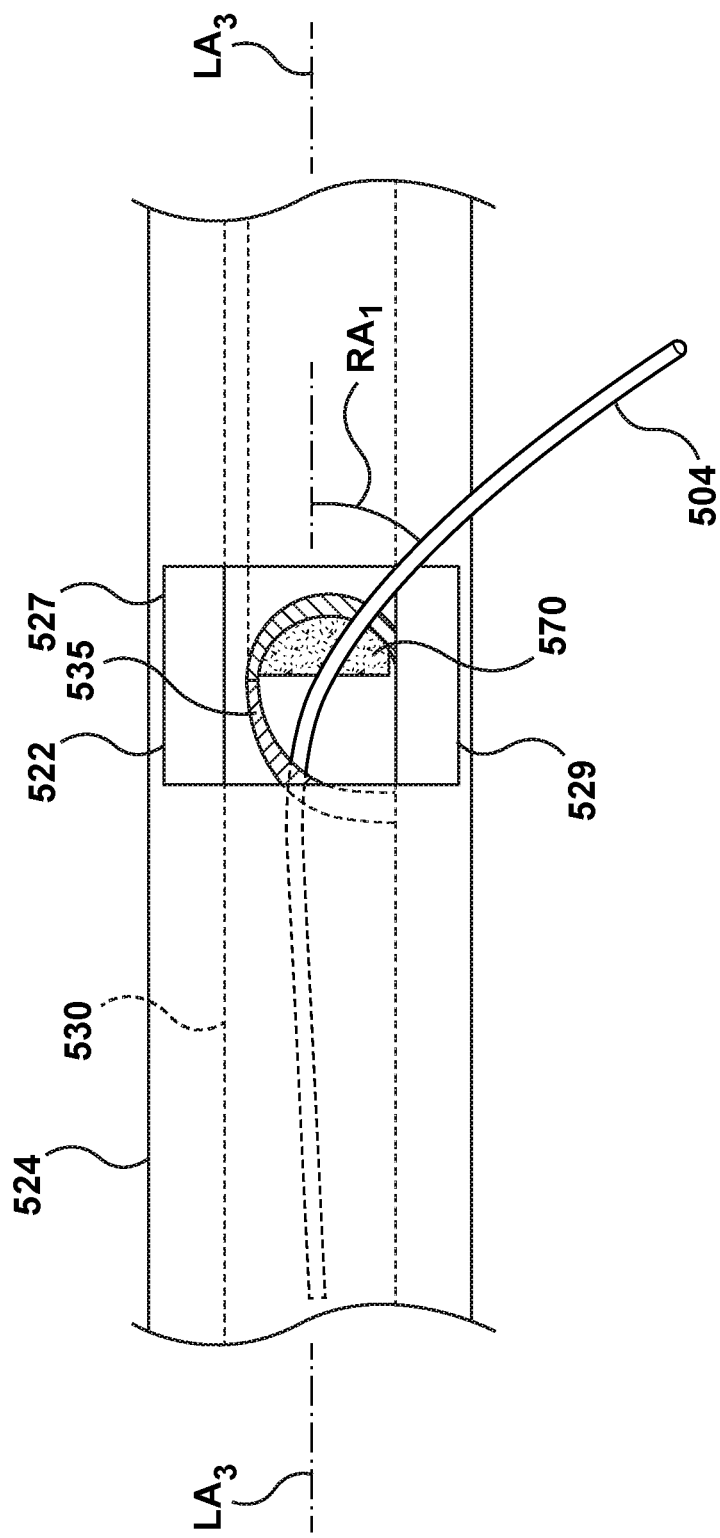

FIGS. 12A and 12B are enlarged planar side views of the catheter 500 of FIGS. 9A and 9B showing a guidewire 504 exiting a selected side port 522 at various rotation angles $RA_1$ in accordance with an embodiment of the present technology. Referring to FIGS. 12A and 12B together, the support structure 524 includes the side port 522, which is shaped or formed as a circumferential slot, disposed therein. The rotation of the wire guide 530 about the longitudinal axis $LA_3$ of the alignment assembly 520 causes the distal guidewire port 535 to be selectively oriented along the circumferential slot of the side port 522. For example, a counterclockwise rotation of the wire guide 530 about the longitudinal axis $LA_3$ positions the distal guidewire port 535 towards a first end 527 of the circumferential slot of the side port 522 (FIG. 12A), while a clockwise rotation of the wire guide 530 about the longitudinal axis $LA_3$ positions the distal guidewire port 535 towards a second end 529 of the circumferential slot of the side port 522 (FIG. 12B). In a particular example, the circumferential slot may encompass up to 90° of the outer circumference of the support structure 524 and the rotational angle $RA_1$ at which the guidewire 504 exits the selected side port 522 can be between 0° and 90° with reference to the slot opening. Accordingly, the alignment assembly 520 can provide a clinician control over the angle of rotation $RA_1$ as well as selection of which side port 522 from a plurality of spaced apart side ports best aligns a guidewire path across the aortic valve AV.

Figure 13:
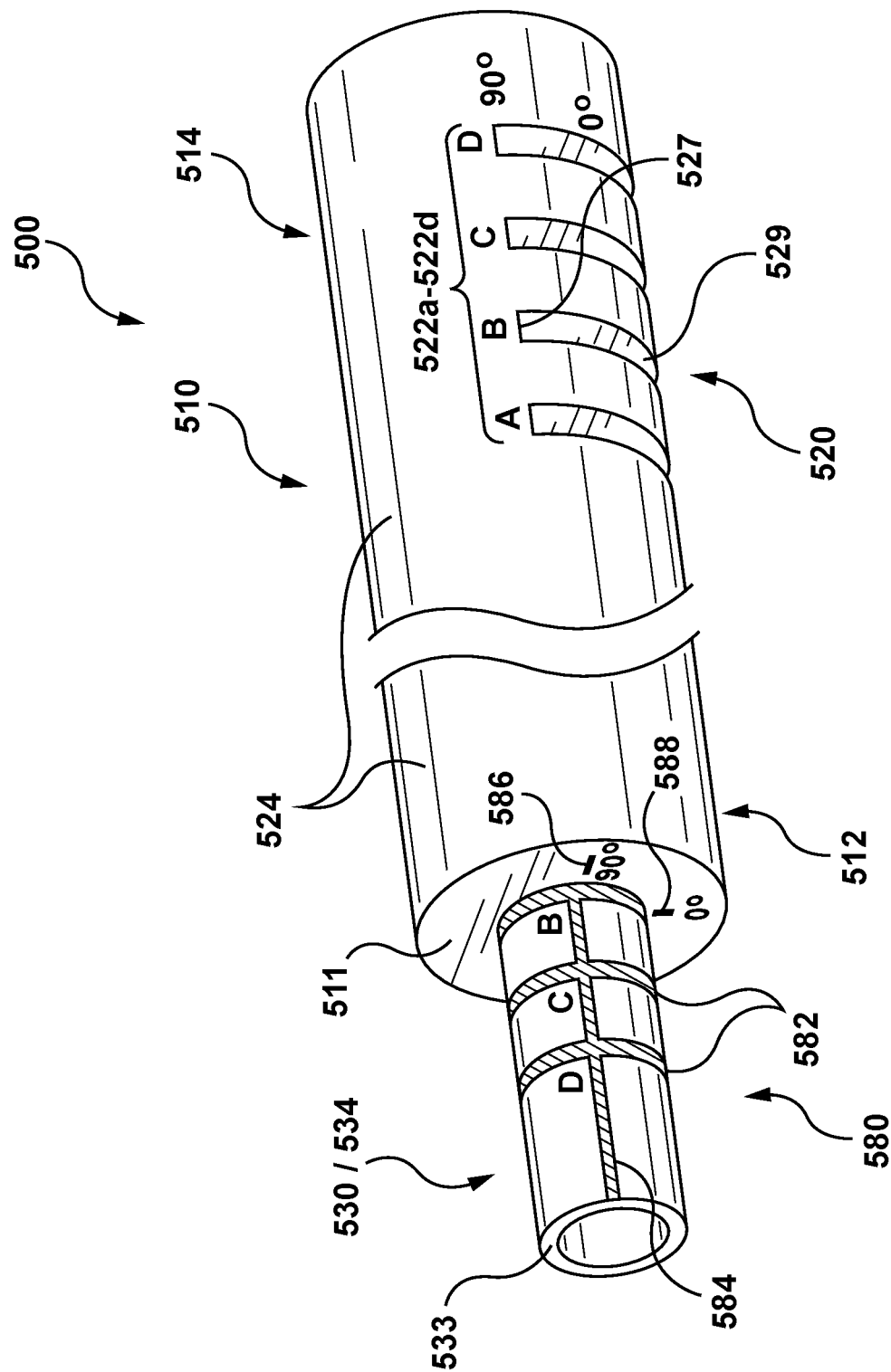
FIG. 13 is a perspective view of the catheter assembly shown in FIG. 9A illustrating an alignment guide disposed on a first portion of the wire guide in accordance with another embodiment hereof.

FIG. 13 is a perspective view of the catheter 500 shown in FIG. 9A illustrating an alignment guide 580 disposed on an outer surface the first portion 534 of the wire guide 530 in accordance with another embodiment hereof. As illustrated in FIG. 13, the alignment guide 580 provides a visual representation of the position of the distal guidewire port 535 (shown in FIGS. 9B and 10) relative to the plurality of spaced-apart side ports 522a-d on the support structure 524. In the example illustrated in FIG. 13, the alignment guide 580 can communicate to the clinician which of the plurality of side ports 522 that the wire guide 530 (and thereby the guidewire 504) is currently aligned with using the circumferential indicator lines 582b-d (and line 582a, not shown). Alignment of the circumferential indicator lines 582 with the proximal end 511 of the support structure 524, or proximal face, surface or edge thereof, can communicate to the clinician which of the side ports 522a-522d is currently aligned with the distal guidewire port 535. In the illustrated example, the distal guidewire port 535 (not visible in FIG. 13) is aligned with side port 522b as indicated by the line 582b at the proximal end 511 of the support structure 524.

The alignment guide 580 may also provide rotation indicator lines 584 for selecting a rotation angle $RA_1$ (FIGS. 12A and 12B) for aligning the distal guidewire port 535 within a circumferential slot of the selected side port (e.g., side port 522b). In the illustrated example, the alignment guide 580 can have a longitudinal rotation indicator line 584 that is substantially aligned with the distal guidewire port 535 (FIGS. 9B and 10) at the second portion (not shown). Likewise the proximal end 511 of the tubular component 510 can include a first rotation indicator marker 586 generally aligned with the first end 527 of the circumferential slots of the side ports 522a-522d, and a second rotation indicator marker 588 generally aligned with the second end 529 of the circumferential slots of the side ports 522a-522d. By rotationally adjusting the wire guide 530 such that the longitudinal rotation indicator line 584 is between the first rotation indicator marker 586 and second rotation indicator marker 588, the guidewire 504 (not shown) can exit the aligned side port 522b at one of various selected rotation angles $RA_1$ (by example, rotation angles $RA_1$ as shown in FIGS. 12A and 12B). In operation, a guidewire (not shown) can be received at the proximal guidewire port 533 and be advanced through the wire guide 530 to exit the distal guidewire port 535 and through a side port (e.g., side port 522a-522d) as selected using the alignment guide 580. A clinician can use image guidance to determine where the aortic valve AV is in relationship to one or more side ports 522 (FIG. 10), and then further use the alignment guide 580 to facilitate delivery of guidewire 504 in the pre-selected manner.

Figure 14A:
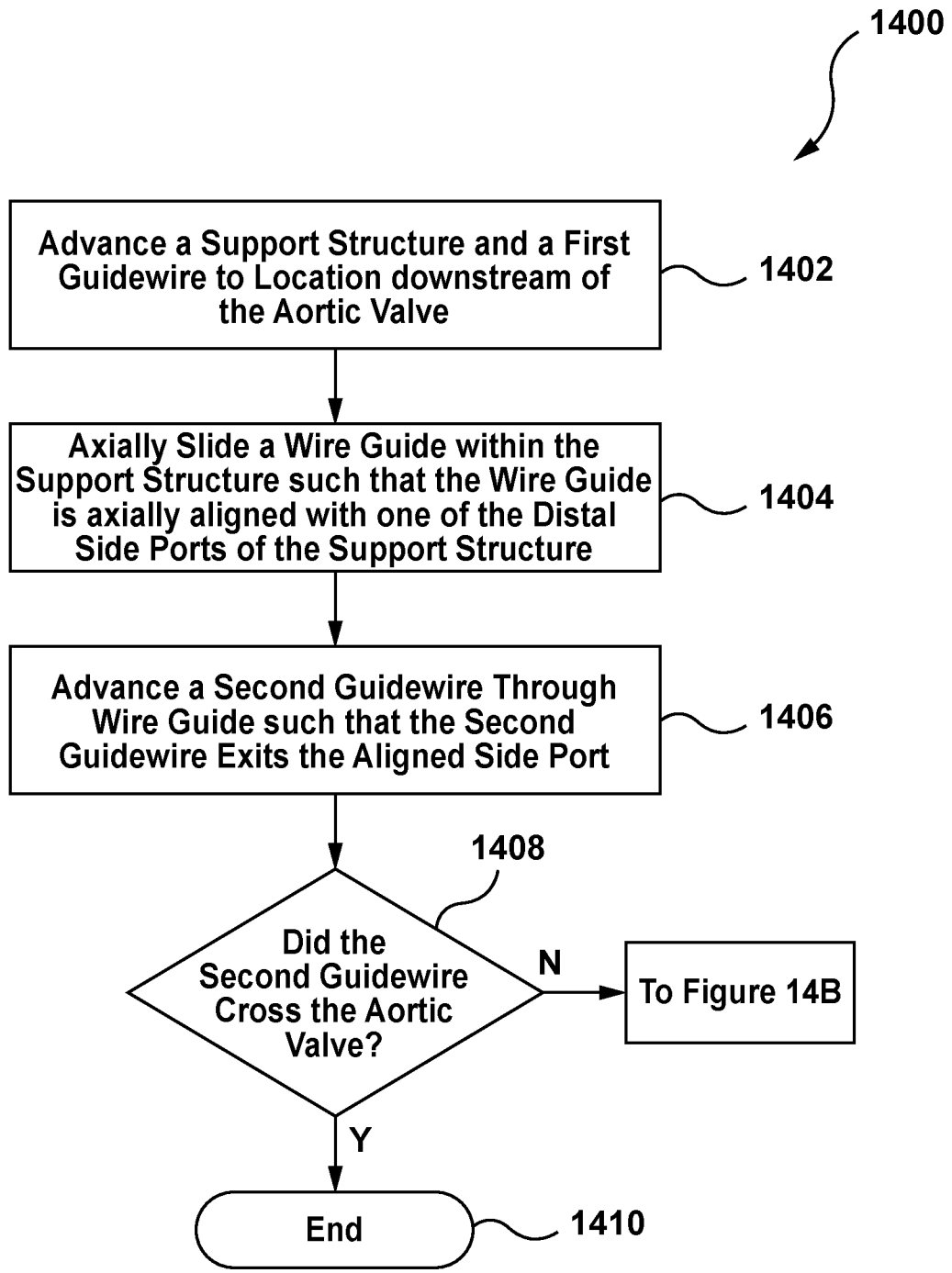
FIG. 14A is a flow diagram illustrating a method for crossing an aortic valve with a guidewire in a patient using the catheter of FIG. 9A and in accordance with an embodiment hereof.

FIG. 14A is block diagram illustrating a method 1400 for crossing an aortic valve with a guidewire in a patient using the catheter 500 of FIG. 9A and in accordance with an embodiment hereof. Referring to FIG. 14A (and with additional reference to FIGS. 9A-13), the method 1400 can include advancing a support structure 524 and a first guidewire 502 through the vasculature of a patient to a location downstream of the aortic valve (block 1402). In one embodiment, the first guidewire 502 is disposed in a proximal segment 512 and a distal segment 514 of the tubular component 510 and/or support structure 524.

The method 1400 can also include axially sliding a wire guide 530 within the support structure 524 such that a distal guidewire port 535 of the wire guide 530 is axially aligned with one of a plurality of side ports 522 disposed in the distal segment 514 of the support structure 524 (block 1404). The method 1400 can further include advancing a second guidewire 504 distally through the wire guide 530 such that the second guidewire 504 exits the aligned side port 522 of the support structure 524 towards the leaflets of the aortic valve (block 1406). In one embodiment, the advancing step is performed during systole of the cardiac cycle (e.g., when the leaflets of the aortic valve are substantially open). In certain embodiments, the first guidewire 502 can be a J-tip guidewire for positioning the catheter 500 at the target location proximal to the aortic valve and the second guidewire 504 is a straight-tip guidewire for crossing the aortic valve.

Following the step of advancing the second guidewire 504 (block 1406), a clinician can assess if the second guidewire successfully crosses the aortic valve (decision block 1408). If the clinician determines that the second guidewire 504 crosses the aortic valve, the method 1400 can end (block 1410). In some embodiments, the catheter 500 can be removed from the patient after crossing the aortic valve with the second guidewire 504. If the second guidewire 504 did not advance between the leaflets of the aortic valve, the process can continue with method 1450 as illustrated in FIG. 14B (with additional reference to FIGS. 9A-11).

Figure 14B:
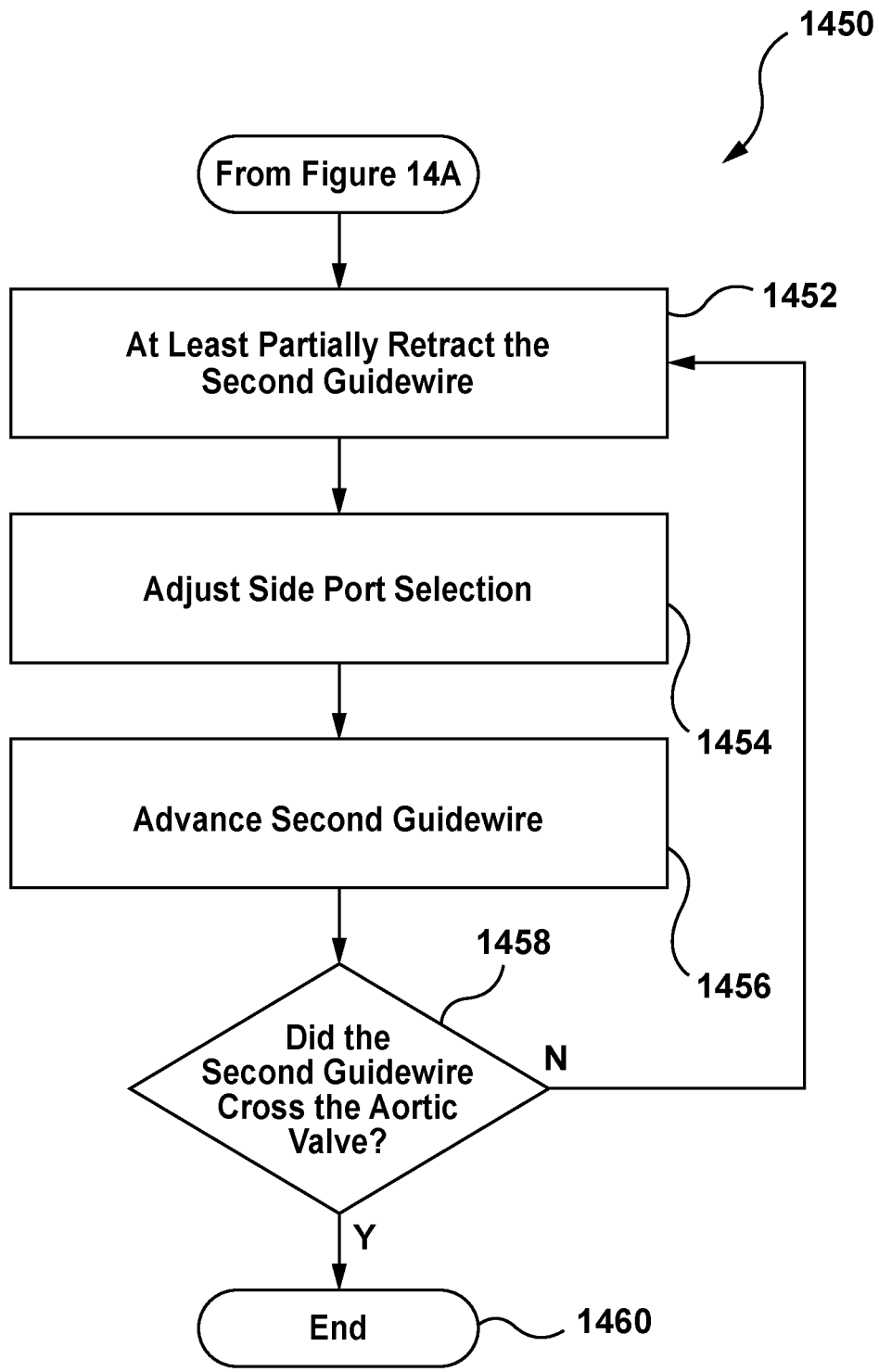
FIG. 14B is a flow diagram illustrating another method for crossing the aortic valve with a guidewire in a patient using the catheter of FIG. 9A and in accordance with an embodiment hereof.

Referring to FIG. 14B, the method 1450 can include at least partially retracting the second guidewire 504 (block 1452) and adjusting the location of the distal opening of the wire guide 530 relative to the support structure 524 to change at least one of the aligned side port 522 and a rotational angle along circumference of the support structure 524 (block 1454). In one embodiment, a clinician can realign the distal guidewire port 535 with another side port 522, or in another embodiment, change a rotational angle $RA_1$ by pushing or pulling and/or rotating the wire guide 530 within the support structure 524. By adjusting the aligned side port 522 and/or the angle of rotation, the guidewire path from the side port 522 can be substantially aligned with the aortic valve (e.g., a leaflet coaptation region). After the adjusting step, the method 1450 can include advancing the second guidewire 504 again (block 1456). Following the step of advancing the second guidewire 504 (block 1456), the clinician can again assess if the second guidewire 504 successfully crosses the aortic valve (decision block 1458). If the clinician determines that the second guidewire 504 crosses the aortic valve, the method 1450 can end (block 1460). If the second guidewire 504 did not advance between the leaflets of the aortic valve, the process can continue back to block 1452 with at least partially retracting the second guidewire and block 1454 with adjusting the location of the distal opening of the wire guide 530 relative to the support structure 524 (as illustrated in FIG. 14B), and the method 1450 concludes (block 1458) when the second guidewire crosses the aortic valve. Following advancement of the second guidewire 504 between the leaflets of the aortic valve, the catheter 500 can be retracted through the vasculature and removed from the patient.

Additional Embodiments

Features of the catheters, catheter assemblies and guidewire delivery system components described above and illustrated in FIGS. 3-14B can be modified to form additional embodiments configured in accordance herewith. For example, the catheters 200, 300 and 400 can include a plurality of side ports and side port selection means such as those described with reference to the catheter apparatus 500 illustrated in FIGS. 9A-11. Similarly, the support structure of the catheter 500 illustrated in FIGS. 9A-11 can have preformed or shape set features, such as bends, loops, coils or spirals for orienting the plurality of side ports towards the targeted heart valve. Additionally, catheters having only one guidewire lumen can be provided with more than one lumen and catheters shown having more than one lumen for slidably receiving a guidewire can be provided with a single lumen. Furthermore, while the catheters described above are discussed as being suitable for delivering a guidewire across an aortic valve, it will be understood that the catheters can also be suitable for delivering guidewires across other heart valves (e.g., mitral valve, tricuspid valve, etc.). Various arrangements of the catheter assemblies described herein may also be used to deliver other therapeutic or medical tools within body lumens. For example, targeted and/or aligned delivery of intraluminal camera devices, surgical tools, prosthetic devices, etc. are contemplated with described alignment assemblies.

Various method steps described above for delivery of the guidewire across a heart valve (e.g., an aortic valve) of a patient also can be interchanged to form additional embodiments of the present technology. For example, while the method steps described above are presented in a given order, alternative embodiments may perform steps in a different order. The various embodiments described herein may also be combined to provide further embodiments.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of crossing an aortic valve, the method comprising:
advancing a support structure and a first guidewire through the vasculature of a patient to a location downstream of the aortic valve, wherein the first guidewire is disposed in a proximal segment and a distal segment of the support structure;

axially sliding a wire guide within the support structure such that a distal opening of the wire guide is axially aligned with one of a plurality of side ports disposed in the distal segment of the support structure; and advancing a second guidewire distally through the wire guide such that the second guidewire exits the aligned side port of the support structure towards the leaflets of the aortic valve.

2. The method of claim 1, wherein the step of advancing the second guidewire towards the leaflets is performed during systole, and wherein the method further comprises:

determining whether the step of advancing the second guidewire caused the second guidewire to traverse between the leaflets to an upstream side of the leaflets;

if the second guidewire did not advance between the leaflets, adjusting the location of the distal opening of the wire guide relative to the support structure to change at least one of the aligned side port and a rotational angle along a circumference of the support structure;

after adjusting the location of the distal opening, advancing the second guidewire again; and repeating determining, adjusting, and advancing steps until the second guidewire traverses between the leaflets to the upstream side of the leaflets.

3. The method of claim 2, wherein after advancing the second guidewire between the leaflets to the upstream side of the leaflets, the method further includes removing the wire guide and the support structure from the vasculature of the patient.

4. The method of claim 1, wherein after advancing the support structure to the location downstream of the aortic valve, axial sliding of the wire guide relative to the support structure includes pulling or pushing the wire guide at a proximal portion.

5. The method of claim 1, wherein prior to axially sliding the wire guide within the support structure, the method includes determining which side port of the plurality of side ports would allow the second guidewire to advance towards the leaflets of the aortic valve in a manner that would atraumatically traverse between the leaflets to the upstream side of the leaflets.

6. The method of claim 5, wherein the wire guide has an alignment guide disposed on an outer surface at a proximal portion, wherein the alignment guide is adapted to remain outside the body of the patient, wherein the alignment guide provides a visual representation of the position of the distal opening relative to the plurality of side ports on the support structure, and wherein the step of axially sliding the wire guide within the support structure includes moving the proximal portion of the wire guide to a marker on the alignment guide that corresponds to the determined side port.

7. The method of claim 6, wherein each of the plurality of side ports comprise a partial circumferential slot, wherein the alignment guide includes indicators that correspond to a degree of rotation of the distal opening relative to each of the partial circumferential slots, and wherein the method further includes:

determining the degree of rotation along the partial circumferential slot of the determined side port that would allow the second guidewire to advance towards the leaflets of the aortic valve; and rotating the wire guide relative to the support structure to the determined degree of rotation using the indicators on the alignment guide.

8. The method of claim 1, wherein the second guidewire is advanced between the leaflets to an upstream side of the aortic valve.

* * * * *